US009186327B2

(12) United States Patent
Davis et al.

(10) Patent No.: US 9,186,327 B2
(45) Date of Patent: *Nov. 17, 2015

(54) CARRIER NANOPARTICLES AND RELATED COMPOSITIONS, METHODS AND SYSTEMS

(71) Applicant: CALIFORNIA INSTITUTE OF TECHNOLOGY, Pasadena, CA (US)

(72) Inventors: Mark E. Davis, Pasadena, CA (US); Akinleye Alabi, Cambridge, MA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/509,118

(22) Filed: Oct. 8, 2014

(65) Prior Publication Data

US 2015/0031832 A1 Jan. 29, 2015

Related U.S. Application Data

(60) Continuation of application No. 13/852,303, filed on Mar. 28, 2013, which is a division of application No. 12/540,319, filed on Aug. 12, 2009, now Pat. No. 8,557,292.

(60) Provisional application No. 61/188,855, filed on Aug. 13, 2008.

(51) Int. Cl.
| A61K 31/765 | (2006.01) |
| A61K 9/14 | (2006.01) |
| C08G 59/40 | (2006.01) |
| A61K 9/51 | (2006.01) |
| A61K 31/4745 | (2006.01) |
| A61K 47/48 | (2006.01) |
| A61K 31/337 | (2006.01) |
| A61K 31/704 | (2006.01) |

(52) U.S. Cl.
CPC ................ *A61K 9/14* (2013.01); *A61K 9/5146* (2013.01); *A61K 31/337* (2013.01); *A61K 31/4745* (2013.01); *A61K 31/704* (2013.01); *A61K 47/48207* (2013.01); *A61K 47/48907* (2013.01); *C08G 59/4078* (2013.01)

(58) Field of Classification Search
CPC .................................................. C08G 59/4078
See application file for complete search history.

(56) References Cited

U.S. PATENT DOCUMENTS

| 4,631,190 | A | 12/1986 | Shen et al. |
| 5,693,631 | A | 12/1997 | Whittemore et al. |
| 6,034,081 | A | 3/2000 | Whittemore et al. |
| 6,048,736 | A | 4/2000 | Kosak |
| 6,060,466 | A | 5/2000 | Whittemore et al. |
| 7,018,609 | B2 | 3/2006 | Pun et al. |
| 7,091,192 | B1 | 8/2006 | Davis et al. |
| 7,166,302 | B2 | 1/2007 | Pun et al. |
| 7,270,808 | B2 | 9/2007 | Cheng et al. |
| 7,427,605 | B2 | 9/2008 | Davis et al. |
| 2002/0061288 | A1 | 5/2002 | Hubbell et al. |
| 2003/0055212 | A1 | 3/2003 | Freund et al. |
| 2003/0059399 | A1 | 3/2003 | Holmes-Farley et al. |
| 2004/0126838 | A1 | 7/2004 | DeFrees et al. |
| 2004/0220146 | A1 | 11/2004 | Freeman et al. |
| 2006/0078997 | A1 | 4/2006 | Lugade et al. |
| 2006/0134062 | A1 | 6/2006 | Huval et al. |
| 2006/0153907 | A1 | 7/2006 | Zalipsky et al. |
| 2006/0159736 | A1 | 7/2006 | Zalipsky et al. |
| 2006/0263435 | A1 | 11/2006 | Davis et al. |
| 2008/0099172 | A1 | 5/2008 | Pelton et al. |
| 2009/0169638 | A1 | 7/2009 | Davis et al. |
| 2010/0029545 | A1 | 2/2010 | Sumerlin et al. |
| 2010/0040556 | A1 | 2/2010 | Davis et al. |
| 2010/0069500 | A1 | 3/2010 | Dhal et al. |
| 2010/0166865 | A1 | 7/2010 | Kumar et al. |
| 2012/0225129 | A1 | 9/2012 | Eliasof et al. |
| 2012/0259021 | A1 | 10/2012 | Jiang et al. |
| 2012/0309691 | A1 | 12/2012 | Zhou et al. |
| 2012/0328564 | A1 | 12/2012 | Govindan et al. |
| 2014/0249203 | A1 | 9/2014 | Davis et al. |
| 2014/0348754 | A1 | 11/2014 | Wiley et al. |

FOREIGN PATENT DOCUMENTS

| WO | WO 97/047658 | 12/1997 |
| WO | WO 99/010022 | 3/1999 |
| WO | WO 2005/119255 | 12/2005 |
| WO | WO 2007/034479 | 3/2007 |
| WO | WO 2007/061919 | 5/2007 |
| WO | WO 2008/011561 | 1/2008 |
| WO | WO 2009/036022 | 3/2009 |
| WO | WO 2010/019718 | 2/2010 |
| WO | WO 2011/072133 | 6/2011 |
| WO | WO 2011/159161 | 12/2011 |
| WO | WO 2012/158622 | 11/2012 |

OTHER PUBLICATIONS

Ahnet al, "Soluble Polymer-Supported Convergent Parallel Library Synthesis", The Royal Society of Chemistry, 2003, 480-481.
Allen, T.M. Ligand-Targeted Therapeutics in Anticancer Therapy, Nature, Oct. 2002, 2, 750-763.
Altieri et al., "Neutron Autoradiography Imaging of Selective Boron Uptake in Human Metastatic Tumours", Appl. Radiat. Isotopes, 2008, 66, 1850-1855.
Armstrong et al., "The Hydrodynamic Radii of Macromolecules and Their Effect on Red Blood Cell Aggregation", Biophysical Journal, 2004, 87(6), 4259-4270.
Bartlett et al., "Impact of Tumor-Specific Targeting on the Biodistribution and Efficacy of siRNA Nanoparticles Measured by Multimodality in Vivo Imaging", P. Natl. Acad. Sci. USA, 2007, 104, 15549-15554.
Bartlett et al., "Physicochemical and Biological Characterization of Targeted, Nucleic Acid-Containing Nanoparticles", Bioconjugate Chemistry, 2007, 18, 456-468.

(Continued)

*Primary Examiner* — Paul Dickinson
(74) *Attorney, Agent, or Firm* — Baker & Hostetler LLP

(57) ABSTRACT

Carrier nanoparticles comprising a polymer containing a polyol coupled to a polymer containing a boronic acid, configured to present the polymer containing a boronic acid to an environment external to the nanoparticle and related compositions, methods and systems.

26 Claims, 15 Drawing Sheets

(56) References Cited

OTHER PUBLICATIONS

Bellocq et al., "Transferrin-Containing Cyclodextrin Polymer-Based Particles for Tumor-Targeted Gene Delivery", Bioconjug Chem, 2003, 14, 1122-1132.

China Patent Application No. 200980131484.0: Office Action dated Feb. 21, 2011, 5 pages, with English translation attached.

Coderre et al., "The Radiation Biology of Boron Neutron Capture Therapy", Radiat. Res., 1999, 151, 1-18.

Choi et al., "Mechanism of Active Targeting in Solid Tumors With Transferrin-Containing Gold Nanoparticles", Natl Acad Sci, 2010, 107(3), 1235-1240.

Choi et al., "Targeting Kidney Mesangium by Nanoparticles of Defined Size", P Natl Acad Sci, 2001, 108,6656-6661.

Dautry-Varsat et al., "pH and the Recycling of Transferrin During Receptor-Mediated Endocytosis", Natl Acad Sci, 1983, 80, 2258-2262.

Davis et al., "Evidence of RNAi in Humans from Systematically Administered siRNA Via Targeted Nanoparticles", Nature, 2010, 1067-1071.

Davis et al., "Nanoparticle Therapeutics: An Emerging Treatment Modality for Cancer", Nature Rev., 2008, 7, 771-782.

Davis, "The First Targeted Delivery of siRNA in Humans Via a Self-Assembling, Cyclodextrin Polymer-Based Nanoparticle: From Concept to Clinic", Molecular Pharm., 2009, 6(3), 659-668.

Duncan, R., "Polymer Conjugates as Anticancer Nanomedicines", Nature Reviews, Sep. 2006, 6, 688-701.

European Patent Application No. 09807260: Office Action dated Jun. 24, 2013, 6 pages.

Friden et al., "Characterization, Receptor Mapping and Blood-Brain Barrier Transcytosis of Antibodies to the Human Transferrin Receptor", J Pharm Exp Ther, 1996,278, 1491-1498.

Fujita, N. et al., "Boronic Acids in Molecular Self-Assembly", Chem. Asian J., 2008, 3, 1076-1091.

Gatter et al., "Transferrin Receptors in Human Tissues: Their Distribution and Possible Clinical Relevance", 1983, J. Clin. Pathol., 539-545.

Goldman, C.K. et al., "In Vitro and In Vivo Gene Delivery Mediated by a Synthetic Polycationic Amino Polymer", Nature Biotechnology, May 1997, 15, 462-466.

Hans, "Targeted Nanoparticles Assembled via Complexation of Boronic-2 Acid-Containing Targeting Moieties to Diol-Containing Polymers", Bioconjugate Chem., Mar. 2013, 1-9.

Hou et al., "Development of Zeptomole and Attomolar Detection Sensitivity of Biotin-Peptide Using a Dot-Blot GoldNanoparticle Immunoassay", Anal. Chem., 2007, 79(3), 980-985.

International Patent Application No. PCT/US2009/053620: Search Report and Written Opinion dated Apr. 2, 2010, 11 pages.

International Patent Application No. PCT/US14/00099: International Search Report and Written Opinion dated Aug. 19, 2014, 17 pages.

Malek et al., "In Vivo Pharmacokinetics, Tissue Distribution and Underlying Mechanisms of Various PEI(-PEG)/siRNA Complexes", Toxicology and Applied Pharmacology, 2009, 236, 97-108.

Merkel et al., "Stability of siRNA Polyplexes from Poly(ethylenimine) and Poly(ethylenimine)—g-poly(ethlene glycol) Under in Vivo Conditions: Effects on Pharmacokinetics and Biodistribution Measured by Fluorescence Fluctuation Spectroscopy and Single Photon Emission Computed Tomography (SPECT) Imaging", Journal of Controlled Release, 2009, 138, 148-159.

Mikado et al., "Application of Neutron Capture Autoradiography to Boron Delivery Seeking Techniques for Selective Accumulation of Boron Compounds to Tumor with Infra-Arterial Administration of Boron Entrapped Water-in-Oil-Water Emulsion", NucIInstrum. Meth. A, 2009, 605, 171-174.

Ogura et al., "Neutron Capture Autoradio Graphic Study of the Biodistribution of B-10 in Tumor-Bearing Mice", Appl. Radiat. Isotopes, 2004, 61, 585-590.

Reineke et al., "Structural Effects of Carbohydrate-Containing Polycations on Gene Delivery. 1. Carbohydrate Size and its Distance from Charge Centers", Bioconjugate Chem, 2003, 14, 247-254.

Smith et al., "Quantitative Imaging and Microlocalization of Boron-10 in Brain Tumors and Infiltrating Tumor Cells by SIMS ion Microscopy: Relevance to Neutron Capture Therapy", Cancer Research, 2001, 61, 8179-8187.

Wittig et al., "Boron Analysis and Boron Imaging in Biological Materials for Boron Neutron Capture Therapy (BNCT)", Grit Rev Oneal Hemat, 2008, 68, 66-90.

Jiang et al., "Nanoparticle-Mediated Cellular Response is Size-Dependent", Nature Nanotech, 2008, 3(3), 145-150.

Kamaly et al., "Targed Polymeric Therapeutic Nanoparticles: Design, Development and Clinical Translation", Chem Soc. Rev, 2012, 41, 2971.

Lockman et al., "Nanoparticle Surface Charges Alter Blood-Brain Barrier Integrity and Permeability", J Drug Target, 2004, 12(9-10), 635-641.

Lundqvist et al., "Nanoparticle Size and Surface Properties Determine the Protein Corona with Possible Implications for Biological Impacts", P Natl Acad Sci, 2008, 105, 14265-14270.

Mangani et al., "EXAFS Studies on Copper Transferrin", J Inorganic Biochem, 1992, 48(1), 33-40.

Martinez-Veracoechea et al., "Desining Super Selectivity in Multivalent Nano-Particle Binding", P Natl Acad Sci USA, 2011, 108(27), 10963-10968.

Montet et al., Multivalent Effects of RGD Peptides Obtained by Nanoparticle Display, J. Med. Chem., 2006, 49(20), 6087-6093.

Nance et al., "A Dense Poly(Ethylene Glycol) Coating Improves Penetration of Large Polymeric Nanoparticles Within Brain Tissue", Sci Transl Med, 2012, 4(149), 149ra119.

Neuwelt et al., "Strategies to Advance Translational Research into Brain Barriers", Lancet Neural, 2008, 7(1), 84-96.

Pardridge, "The Blood-Brain Barrier: Bottleneck in Brain Drug Development", NeuroRX, 2005, 2(1), 3-14.

Perrault et al., "Mediating Tumor Targeting Efficiency of Nanoparticles Through Design", Nano Lett, 2009, 9(5), 1909-1915.

Wiley et al., "Trancytosis and Brain Uptake of Transferrin-Containing Nanoparticles by Tuning Avidity to Transferrin Receptor", P. Natl. Acad. Sci., 2013, 1-6.

Walburg et al., "Epithelial and Endothelial Barriers in the Olfactory Region of the Nasal Cavity of the Rat", Histochem. Cell Bioi, 2008, 130(1), 127-140.

Xiao et al., "The Effect of Surface Charge on In Vivo Biodistribution of PEG-Oiigocholic Acid Based Micellar Nanoparticles", Biomaterials, 2011, 32, 3435-3446.

Japanese Patent Application No. 2011-523150: Office Action dated Jun. 10, 2014, 3 pages.

Japanese Patent Application No. 2011-523150: Office Action dated Oct. 29, 2013.

Liu, Y., et al. "Hydroxyl Stereochemistry and Amine Number within Poly(glycoamidoamine)s Affect Intracellular DNA Delivery", Journal of the American Chemical Society,127, 9, 3004-3015, 2005.

Peer, D. et al., "Nanocarriers as an Emerging Platform for Cancer Therapy", Nature Nanotechnology, Dec. 2007, 2, 751-760.

Pisarev, M.A. et al., "Boron Neutron Capture Therapy in Cancer: Past, Present and Future", 2007, 852-856.

Torchilin, V.P. "TAT Peptide on the Surface of Liposomes Affords Their Efficient Intracellular Delivery Even at Low Temperature and in the Presence of Metabolic Inhibitors", Jul. 17, 2001, PNAS, 98(15),15,8786-8791.

Vicent, M.J. et al., "Polymer Conjugates: Nanosized Medicines for Treating Cancer", Trends in Biotechnology, Jan. 2006, 24(1), 40-47.

Wakabayashi et al, "Affinity-Labeling-Based Introduction of a Reactive Handle for Natural Protein Modification", Chem. Asian. J., 2008, 1134-1139.

Wolf, W. et al., "F-MRS Studies of Fluorinated Drugs in Humans", Advanced Drug Delivery Reviews, 2000, 41, 55-74.

Yu et al., "Boosting Brain Uptake of a Therapeutic Antibody by Reducing Its Affinity for aTranscytosis Target", Sci. Transl. Med., 2011, 3(84), 1-8.

| Polymer | Effective Diameter (nm) | Zeta Potential (mV) |
|---|---|---|
| poly(Mucic Acid-DiCys-PEG) | 4.8 | -5 |
| poly(Mucic Acid-DiCys-PEG)-CPT | 57 | -8 |

FIG. 14

CARRIER NANOPARTICLES AND RELATED COMPOSITIONS, METHODS AND SYSTEMS

CROSS REFERENCE TO RELATED APPLICATIONS

This application is a continuation of U.S. patent application Ser. No. 13/852,303, filed on Mar. 28, 2013, which is divisional application of U.S. U.S. patent application Ser. No. 12/540,319, filed on Aug. 12, 2009, now U.S. Pat. No. 8,557,292, which claims priority to U.S. Provisional Application Ser. No. 61/188,855, filed on Aug. 13, 2008, each of these applications being incorporated by reference herein.

GOVERNMENT RIGHTS

This invention was made with government support under Grant No. CA119347 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 23, 2015, is named 101465.000186_SL.txt and is 1,549 bytes in size.

FIELD

The present disclosure relates to carrier nanoparticles and in particular to nanoparticles suitable for delivering compounds of interest, and related compositions, methods and systems.

BACKGROUND

Effective delivery of compounds of interest to cells, tissues, organs, and organisms has been a challenge in biomedicine, imaging and other fields where delivery of molecules of various sizes and dimensions to a predetermined target is desirable.

Whether for pathological examination, therapeutic treatment or for fundamental biology studies, several methods are known and used for delivering various classes of biomaterials and biomolecules which are typically associated with a biological and/or chemical activity of interest.

As the number of molecules suitable to be used as chemical or biological agents (e.g. drugs, biologics, therapeutic or imaging agents) increases, development of a delivery systems suitable to be used with compounds of various complexity, dimensions and chemical nature has proven to be particularly challenging.

Nanoparticles are structures useful as carriers for delivering agents with various methods of delivery. Several nanoparticle delivery systems exist, which utilize an array of different strategies to package, transport, and deliver an agent to specific targets.

SUMMARY

Provided herein are nanoparticles and related compositions, methods and systems that in several embodiments provide a multifunctional tool for effective and specific delivery of a compound of interest. In particular, in several embodiments, nanoparticles herein described can be used as a flexible system for carrying and delivering a wide range of molecules of various sizes, dimensions and chemical nature to predetermined targets.

According to a first aspect, a nanoparticle comprising a polymer containing a polyol and to a polymer containing a boronic acid is described. In the nanoparticle, the polymer containing a boronic acid is coupled to the polymer containing a polyol and the nanoparticle is configured to present the polymer containing a boronic acid to an environment external to the nanoparticle. In the nanoparticle one or more compounds of interest can be carried by the nanoparticle, as a part of or attached to the polymer containing a polyol and/or the polymer containing a boronic acid.

According to a second aspect, a composition is described. The composition comprises a nanoparticle herein described and a suitable vehicle and/or excipient.

According to a third aspect, a method to deliver a compound to a target is described. The method comprises contacting the target with a nanoparticle herein described wherein the compound is comprised in the polymer containing a polyol or in the polymer containing a boronic acid of the nanoparticle herein described.

According to a fourth aspect, a system to deliver a compound to a target is described. The system comprises at least a polymer containing a polyol and polymer containing a boronic acid capable of reciprocal binding through a reversible covalent linkage, to be assembled in a nanoparticle herein described comprising the compound.

According to a fifth aspect, a method to administer a compound to an individual is described. The method comprises administering to the individual an effective amount of a nanoparticle herein described, wherein the compound is comprised in the polymer containing a polyol and/or in the polymer containing a boronic acid.

According to a sixth aspect, a system for administering a compound to an individual is described. The system comprises, at least a polymer containing a polyol and polymer containing a boronic acid capable of reciprocal binding through a reversible covalent linkage, to be assembled in a nanoparticle herein described attaching the compound to be administered to the individual according to methods herein described.

According to a seventh aspect, a method to prepare a nanoparticle comprising a polymer containing a polyol and a polymer containing a boronic acid is described. The method comprises contacting the polymer containing polyols with the polymer containing a boronic acid for a time and under condition to allow coupling of the polymer containing polyoly with the polymer containing a boronic acid.

According to an eight aspect, several polymer containing a boronic acid are described which are illustrated in details in the following sections of the present disclosure.

According to a ninth aspect, several polymers containing polyols are described, which are illustrated in details in the following sections of the present disclosure.

Nanoparticles herein described and related compositions, methods, and systems can be used in several embodiments as a flexible molecular structure suitable for carrying compounds of various sizes, dimensions and chemical nature.

Nanoparticles herein described and related compositions, methods, and systems can be used in several embodiments as delivery systems which can provide protection of the carried compound from degradation, recognition by immune system and loss due to combination with serum proteins or blood cells.

Nanoparticles herein described and related compositions, methods, and systems can be used in several embodiments as delivery systems characterized by steric stabilization and/or ability to deliver the compound to specific targets such as tissues, specific cell types within a tissue and even specific intracellular locations within certain cell types.

Nanoparticles herein described and related compositions, methods, and systems can be designed in several embodiments, to release a carried compound in a controllable way, including controlled release of multiple compounds within a same nanoparticle at different rates and/or times.

Nanoparticles herein described and related compositions, methods, and systems can be used in several embodiments, to deliver compounds with enhanced specificity and/or selectivity during targeting and/or enhanced recognition of the compound by the target compared to certain systems of the art.

Nanoparticles herein described and related compositions, methods, and systems can be used in several embodiments in connection with applications wherein controlled delivery of a compound of interest is desirable, including but not limited to medical applications, such as therapeutics, diagnostics and clinical applications. Additional applications comprise biological analysis, veterinary applications, and delivery of compounds of interest in organisms other than animals, and in particular in plants.

The details of one or more embodiments of the disclosure are set forth in the accompanying drawings and the detailed description and examples below. Other features, objects, and advantages will be apparent from the detailed description, examples and drawings, and from the appended claims

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

FIG. 3, shows results of a MAP gel retardation assay with plasmid DNA according to an embodiment of the present disclosure. A DNA ladder is loaded in Lane 1. Lanes 2-8 show plasmid DNA combined with MAP of incrementally increased charge ratio. Charge ratio is defined as the amount of positive charges on the MAP divided by the amount of negative charges on the nucleic acid.

FIG. 4 shows results of a MAP gel retardation assay with siRNA according to an embodiment of the present disclosure. A DNA ladder is loaded in Lane 1. Lanes 2-8 show siRNA combined with MAP of incrementally increased charge ratio.

FIG. 5 shows a diagram illustrating a plot of particle size (determined from dynamic light scattering (DLS) measurements) versus charge ratio and zeta potential (a property that relates to the surface charge of the nanoparticle) versus charge ratio for MAP-plasmid nanoparticles according to an embodiment of the present disclosure.

FIG. 6 shows a diagram illustrating a plot of particle size (DLS) versus charge ratio and zeta potential versus charge ratio for BA-PEGylated MAP-plasmid nanoparticles according to an embodiment of the present disclosure.

FIG. 8 shows a diagram illustrating a plot of relative light units (RLU) that are a measure of the amount of luciferase protein expressed from the pGL3 plasmid that has been delivered to the cells versus charge ratio for a MAP/pGL3 transfection into HeLa Cells according to an embodiment of the present disclosure.

FIG. 9, shows a diagram illustrating a plot of cell survival versus charge ratio after a MAP/pGL3 transfection according to an embodiment of the present disclosure. The survival data are for the experiments shown in FIG. 8.

FIG. 10 shows a diagram illustrating a plot of relative light units (RLU) versus particle type for a co-transfection of MAP Particles containing pGL3 and siGL3 at a charge ratio of 5+/− into HeLa Cells according to an embodiment herein described. The wording siCON indicates an siRNA with a control sequence.

FIG. 11 shows a plot of relative light units (RLU) versus siGL3 concentration for a delivery of MAP/siGL3 at a charge ratio of 5+/− into HeLa-Luc cells according to an embodiment of the present disclosure.

FIG. 12, show a schematic for a synthesis of boronic acid-PEG disulfide-Transferrin according to an embodiment of the present disclosure.

FIG. 13 shows a schematic for a formulation of a nanoparticle with Campothecin Mucic acid polymer (CPT-mucic acid polymer) in water according to an embodiment of the present disclosure.

FIG. 14 shows a table summarizing particle sizes and zeta potentials of nanoparticles formed from the CPT-mucic acid polymer conjugated in water, prepared according to an embodiment of the present disclosure.

FIG. 15 shows a formulation of a boronic acid-PEGylated nanoparticle with CPT-Mucic Acid Polymer and boronic acid-disulfide-PEG$_{5000}$ in water according to an embodiment of the present disclosure.

DETAILED DESCRIPTION

Figure 1:
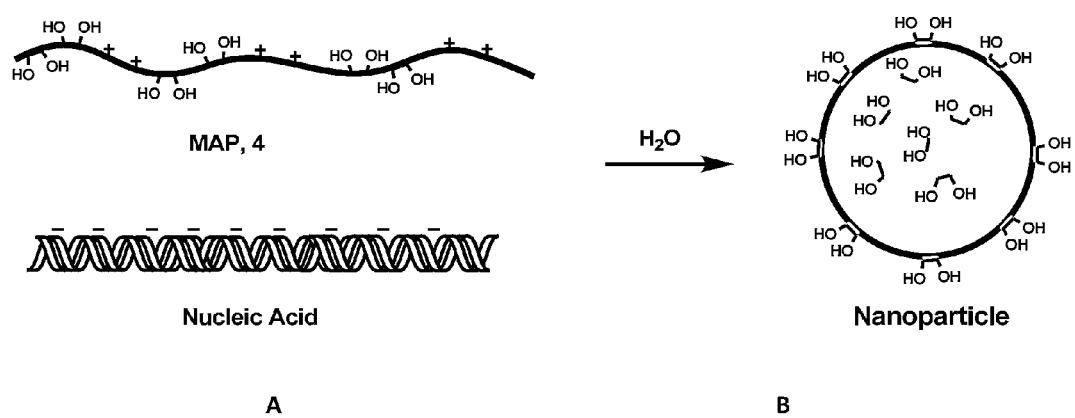
FIG. 1 shows a schematic representation of a nanoparticle and a related method for the relevant formation in absence of a boronic acid containing compound. Panel A shows a schematic representation of a polymer containing a polyol (MAP, 4) and a compound of interest (nucleic acid) according to an embodiment herein described. Panel B shows a nanoparticle formed upon assembly of the polymer containing a polyol and compound shown in panel A.

Provided herein are nanoparticles and related compositions, methods, and systems that can be used in connection for delivering a compound of interest (herein also cargo) comprised in the nanoparticles.

The term "nanoparticle" as used herein indicates a composite structure of nanoscale dimensions. In particular, nanoparticles are typically particles of a size in the range of from about 1 to about 1000 nm, and are usually spherical although different morphologies are possible depending on the nanoparticle composition. The portion of the nanoparticle contacting an environment external to the nanoparticle is generally identified as the surface of the nanoparticle. In nanoparticles herein described, the size limitation can be restricted to two dimensions and so that nanoparticles herein described include composite structure having a diameter from about 1 to about 1000 nm, where the specific diameter depends on the nanoparticle composition and on the intended use of the nanoparticle according to the experimental design. For example, nanoparticles to be used in several therapeutic applications typically have a size of about 200 nm or below, and the ones used, in particular, for delivery associated to cancer treatment typically have a diameter from about 1 to about 100 nm.

Additional desirable properties of the nanoparticle, such as surface charges and steric stabilization, can also vary in view of the specific application of interest. Exemplary properties that can be desirable in clinical applications such as cancer treatment are described in Davis et al, 2008, Duncan 2006 and Allen 2002 each incorporated herein by reference in its entirety. Additional properties are identifiable by a skilled person upon reading of the present disclosure. Nanoparticle dimensions and properties can be detected by techniques known in the art. Exemplary techniques to detect particles dimensions include but are not limited to dynamic light scattering (DLS) and a variety of microscopies such at transmission electron microscopy (TEM) and atomic force microscopy (AFM). Exemplary techniques to detect particle morphology include but are not limited to TEM and AFM. Exemplary techniques to detect surface charges of the nanoparticle include but are not limited to zeta potential method. Additional techniques suitable to detect other chemical properties comprise by $^1$H, $^{11}$B, and $^{13}$C and $^{19}$F NMR, UV/Vis and infrared/Raman spectroscopies and fluorescence spectroscopy (when nanoparticle is used in combination with fluorescent labels) and additional techniques identifiable by a skilled person.

Nanoparticles and related compositions, methods, and systems herein described can be used to deliver a compound of interest and in particular an agent to a predetermined target.

The term "deliver" and "delivery" as used herein indicates the activity of affecting the spatial location of a compound, and in particular controlling said location. Accordingly, delivering a compound in the sense of the present disclosure indicates the ability to affect positioning and movement of the compound at a certain time under a certain set of conditions, so that the compound's positioning and movement under those conditions are altered with respect to the positioning and movement that the compound would otherwise have.

In particular, delivery of a compound with respect to a reference endpoint indicates the ability to control positioning and movement of the compound so that the compound is eventually positioned on the selected reference endpoint. In an in vitro system, delivery of a compound is usually associated to a corresponding modification of the chemical and/or biological detectable properties and activities of the compound. In an in vivo system, delivery of a compound is also typically associated with modification of the pharmacokinetics and possibly pharmacodynamics of the compound.

Pharmacokinetic of a compound indicates absorption, distribution, metabolism and excretion of the compound from the system, typically provided by the body of an individual. In particular the term "absorption" indicates the process of a substance entering the body, the term "distribution" indicates the dispersion or dissemination of substances throughout the fluids and tissues of the body, the term "metabolism" indicates the irreversible transformation of parent compounds into daughter metabolites and the term "excretion" indicates the elimination of the substances from the body. If the compound is in a formulation, pharmacokinetics also comprises liberation of the compound from the formulation which indicates process of release of the compound, typically a drug, from the formulation. The term "pharmacodynamic" indicates physiological effects of a compound on the body or on microorganisms or parasites within or on the body and the mechanisms of drug action and the relationship between drug concentration and effect. A skilled person will be able to identify the techniques and procedures suitable to detect pharmacokinetics and pharmacodynamic features and properties of a compound of interest and in particular of an agent of interest such as a drug.

The term "agent" as used herein indicates a compound capable of exhibiting a chemical or biological activity associated to the target. The term "chemical activity" as used herein indicates the ability of the molecule to perform a chemical reaction. The term biological activity as used herein indicates the ability of the molecule to affect a living matter. Exemplary chemical activities of agents comprise formation of a covalent or electrostatic interaction. Exemplary biological activities of agents comprise production and secretion of endogenous molecules, absorption and metabolization of endogenous or exogenous molecules and activation or deactivation of genetic expression including transcription and translation of a gene of interest.

The term "target" as used herein indicates a biological system of interest including unicellular or pluricellular living organisms or any portion thereof and include in vitro or in vivo biological systems or any portion thereof The nanoparticles herein described a polymer containing a boronic acids is coupled to a polymer containing a polyol is arranged in the nanoparticle to be presented to an environment external to the nanoparticle.

The term a "polymer" as used herein indicates a large molecule composed of repeating structural units typically connected by covalent chemical bonds. A suitable polymer may be a linear and/or branched, and can take the form of a homopolymer or a co-polymer. If a co-polymer is used, the co-polymer may be a random copolymer or a branched co-polymer. Exemplary polymers comprise water-dispersible and in particular water soluble polymers. For example, suitable polymers include, but are not limited to polysaccharides, polyesters, polyamides, polyethers, polycarbonates, polyacrylates, etc. For therapeutic and/or pharmaceutical uses and applications, the polymer should have a low toxicity profile and in particular that are not toxic or cytotoxic. Suitable polymers include polymers having a molecular weight of about 500,000 or below. In particular, suitable polymers can have a molecular weight of about 100,000 and below.

The term "polymer containing a polyol" or "polyol(s) polymer" as used herein indicates a polymer presenting multiple hydroxyl functional groups. In particular, the polymer containing a polyol suitable to form the nanoparticles here described comprise polymers presenting at least a portion of the hydroxyl functional groups for a coupling interaction with at least one boronic acid of a polymer containing a boronic acid.

The term "present" as used herein with reference to a compound or functional group indicates attachment performed to maintain the chemical reactivity of the compound or functional group as attached. Accordingly, a functional group presented on a surface, is able to perform under the appropriate conditions the one or more chemical reactions that chemically characterize the functional group.

Structural units forming polymers containing polyols comprise monomeric polyols such as pentaerythritol, ethylene glycol and glycerin. Exemplary polymers containing polyols comprise polyesters, polyethers and polysaccharides. Exemplary suitable polyethers include but are not limited to diols and in particular diols with the general formula HO—$(CH_2CH_2O)_p$—H with p>1, such as polyethylene glycol, polypropylene glycol, and poly(tetramethylene ether) glycol. Exemplary, suitable polysaccharides include but are not limited to cyclodextrins, starch, glycogen, cellulose, chitin and β-Glucans. Exemplary, suitable polyesters include but are not limited to polycarbonate, polybutyrate and polyethylene terephthalate, all terminated with hydroxyl end groups. Exemplary polymers containing polyols comprise polymers of about 500,000 or less molecular weight and in particular from about 300 to about 100,000.

Several polymers containing polyols are commercially available and/or can be produced using techniques and procedures identifiable by a skilled person. Exemplary procedures for the synthesis of an exemplary polyol polymer are described in Liu et al 2005, and others are illustrated in Examples 1-4. Additional procedures for making polymer containing polyols will be identifiable by a skilled person in view of the present disclosure.

The term "polymer containing a boronic acid" or "BA polymer" as used herein indicates polymer containing at least one boronic acid group presented for binding to a hydroxyl group of a polymer containing polyols. In particular, polymers containing boronic acids of the nanoparticles herein described include a polymer comprising in at least one structural unit an alkyl or aryl substituted boronic acid containing a carbon to boron chemical bond. Suitable BA polymers comprise polymers wherein boronic acid is in a terminal structural unit or in any other suitable position to provide the resulting polymer with hydrophilic properties. Exemplary polymers containing polyols comprise polymers of about 40,000 or less molecular weight and in particular of about 20,000 or less, or about 10,000 or less.

Several polymer containing a boronic acids are commercially available and/or can be produced using techniques and procedures identifiable by a skilled person. Exemplary procedures for the synthesis of an exemplary polyol polymer are described in Liu and Reineke (2005) and other new ones are illustrated in Examples 5-8. Additional procedures for making BA polymers will be identifiable by a skilled person in view of the present disclosure.

In the nanoparticles herein described polyols polymers are coupled to the BA polymers. The term "coupled" or "coupling" as used herein with reference to attachment between two molecules indicates an interaction forming a reversible covalent linkage. In particular, in presence of a suitable medium, a boronic acid presented on the BA polymer interact with hydroxyl groups of the polyols via a rapid and reversible pair-wise covalent interaction to form boronic esters in a suitable medium. Suitable medium include water and several aqueous solutions and additional organic media identifiable by a skilled person. In particular, when contacted in an aqueous medium BA polymers and polyols polymers react, producing water as a side product. The boronic acid polyol interaction is generally more favorable in aqueous solutions but is also known to proceed in organic media. In addition, cyclic esters formed with 1,2 and 1,3 diols are generally more stable than their acyclic ester counterparts.

Accordingly, in a nanoparticle herein described, at least one boronic acid of the polymer containing a boronic acid is bound to hydroxyl groups of the polymer containing a polyol with a reversible covalent linkage. Formation of a boronic ester between BA polymers and polyols polymers can be detected by methods and techniques identifiable by a skilled person such as boron-11 nuclear magnetic resonance ($^{11}B$ NMR), potentiomeric titration, UV/Vis and fluorescent detection techniques whereby the technique of choice is dependent on the specific chemical nature and properties of the boronic acid and polyol composing the nanoparticle.

A nanoparticle resulting from coupling interactions of a BA polymer herein described with a polyol polymer herein described presents the BA polymer on the surface of the particle. In several embodiments the nanoparticles can have a diameter from about 1 to about 1000 nm and a spherical morphology although the dimensions and morphology of the particle are largely determined by the specific BA polymer and polyol polymers used to form the nanoparticles and by the compounds that are carried on the nanoparticles according to the present disclosure.

In several embodiments the compound of interest carried by the nanoparticle forms part of the BA polymer and/or the polyol polymers. Examples of such embodiments are provided by nanoparticles wherein one or more atoms of a polymer is replaced by a specific isotope e.g. $^{19}F$ and $^{10}B$, and are therefore suitable as agent for imaging the target and/or providing radiation treatment to the target.

In several embodiments, the compound of interest carried the nanoparticle is attached to a polymer, typically a polyol polymer, through covalent or non covalent linkage. Examples of such embodiments are provided by nanoparticles wherein one or more moieties in at least one of the polyol polymer and BA polymer attaches one or more compounds of interest.

The term "attach", "attached" or "attachment" as used herein, refers to connecting or uniting by a bond, link, force or tie in order to keep two or more components together, which encompasses either direct or indirect attachment such that for example where a first compound is directly bound to a second compound, and the embodiments wherein one or more intermediate compounds, and in particular molecules, are disposed between the first compound and the second compound.

In particular, in some embodiments a compound can be attached to the polyol polymer or BA polymer through covalent linkage of the compound to suitable moieties of the polymer. Exemplary covalent linkages are illustrated in Example 19 where, attachment of the drug Camptothecin to Mucic Acid polymer is performed through biodegradable ester bond linkage, and in Example 9, wherein attachment of transferrin to BA-PEG$_{5000}$ is performed through pegylation of the transferrin.

In some embodiments, the polymer can be designed or modified to enable the attachment of a specific compound of interest, for example by adding one or more functional groups able to specifically bind a corresponding functional group on the compound of interest. For example, in several embodiments it is possible to PEGylate the nanoparticle with a BA-PEG-X, where X can be a Maleimide or an iodoacetyl group or any leaving group that will react specifically with a thiol or non-specifically with an amine. The compound to be attached can then react to the maleimide or iodoacetyl groups after modification to express a thiol functional group. The compound to be attached can also be modified with aldehydes or ketone groups and these can react via a condensation reaction with the diols on the polyols to give acetals or ketals.

In some embodiments, a compound of interest can be attached to the polyol polymer or BA polymer through non covalent bonds such as ionic bonds and intermolecular interactions, between a compound to be attached and a suitable moiety of the polymer. Exemplary non covalent linkages are illustrated in Example 10.

A compound of interest can be attached to the nanoparticle before, upon or after formation of the nanoparticle, for example via modification of a polymer and/or of any attached compound in the particulate composite. Exemplary procedures to perform attachment of a compound on the nanoparticle are illustrated in the Examples section. Additional procedures to attach a compound to a BA polymer polyol polymer or other components of the nanoparticle herein described (e.g. a previously introduced compound of interest) can be identified by a skilled person upon reading of the present disclosure.

In some embodiments, at least one compound of interest attached to a BA polymer presented on the nanoparticle herein described is an agent that can be used as a targeting ligand. In particular, in several embodiments, the nanoparticle attaches on the BA polymer one or more agents to be used as a targeting ligand, and on the polyol polymer and/or the BA polymer, one or more agents to be delivered to a target of choice.

The term "targeting ligand" as used in the present disclosure indicates any molecule that can be presented on the surface of a nanoparticle for the purpose of engaging a specific target, and in particular specific cellular recognition, for example by enabling cell receptor attachment of the nanoparticle. Examples of suitable ligands include, but are not limited to, vitamins (e.g. folic acid), proteins (e.g. transferrin, and monoclonal antibodies), monosaccharides (e.g. galactose), peptides, and polysaccharides. In particular targeting ligands can be antibodies against certain surface cell receptors such as anti-VEGF, small molecules such as folic acid and other proteins such as holo-transferrin.

The choice of ligand, as one of ordinary skill appreciates, may vary depending upon the type of delivery desired. As another example, the ligand may be membrane permeabilizing or membrane permeable agent such as the TAT protein from HIV-1. The TAT protein is a viral transcriptional activation that is actively imported into the cell nucleus. Torchilin, V. P. et al, PNAS. 98, 8786 8791, (2001). Suitable targeting ligands attached to a BA polymer typically comprise a flexible spacer such as a poly(ethylene oxide) with a boronic acid attached to its distal end (see Example 9).

In several embodiments, at least one of the compounds comprised or attached to the polyol polymer and/or BA polymer (including a targeting ligand) can be an agent and in particular a drug, to be delivered to a target, for example an individual, to which the chemical or biological activity, e.g. the therapeutic activity, is to be exerted.

Selection of a polyol polymer and a BA polymer suitable to form a nanoparticle herein described can be performed in view of the compound and the target of interest. In particular, selection of a suitable polymer containing a polyol and a suitable BA polymer to form a nanoparticle herein described can be performed by providing candidate polyol polymers and BA polymer, and selecting the polyol polymer and the BA polymer able to form a coupling interaction in the sense of the disclosure, wherein the selected BA polymer and polyol polymer have a chemical composition such that in view of the compound of interest and targeting ligand to comprised or attached to the polyol polymers and/or the BA polymers, the polyol polymers is less hydrophilic than the BA polymer. Detection of the BA polymer on the surface of the nanoparticle and related presentation on the environment external to the nanoparticle can be performed by detection of the zeta potential which can demonstrate modification of the surface of the nanoparticle as illustrated in Example 12. (see in particular FIG. 6) Additional procedures to detect the surface charge of the particles and the stability of the particles in salt solutions, include detection of changes of the particle size such as the ones exemplified in Example 12 (see in particular FIG. 7) and additional procedures identifiable by a skilled person In several embodiments, polymers containing polyols comprise one or more of at least one of the following structural units

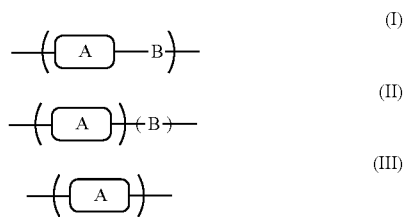

wherein
    A is an organic moiety of formula

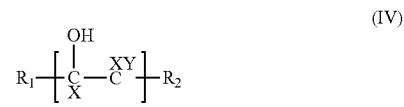

in which
    $R_1$ and $R_2$ are independently selected from any carbon based or organic group with a molecular weight of about 10 kDa or less;
    X is independently selected from an aliphatic group, containing one or more of —H, —F, —C, —N or —O; and
    Y is independently selected from —OH or an organic moiety bearing a hydroxyl (—OH) group including but not limited to —CH$_2$OH, —CH$_2$CH$_2$OH, —CF$_2$OH, —CF$_2$CF$_2$OH, and C(R$_1$G$_1$)(RG$_2$)(R$_1$G$_3$) OH, with R$_1$G$_1$, R$_1$G$_2$ and R$_1$G$_3$ are independently organic based functionalities,
and
    B is an organic moiety linking one of R$_1$ and R$_2$ of a first A moiety with one of the R$_1$ and R$_2$ of a second A moiety.

The term "moiety" as used herein indicates a group of atoms that constitute a portion of a larger molecule or molecular species. In particular, a moiety refers to a constituent of a repeated polymer structural unit. Exemplary moieties include acid or base species, sugars, carbohydrates, alkyl groups, aryl groups and any other molecular constituent useful in forming a polymer structural unit.

The term "organic moiety" as used herein indicates a moiety which contains a carbon atom. In particular, organic groups include natural and synthetic compounds, and compounds including heteroatoms. Exemplary natural organic moieties include but are not limited to most sugars, some alkaloids and terpenoids, carbohydrates, lipids and fatty acids, nucleic acids, proteins, peptides and amino acids, vitamins and fats and oils. Synthetic organic groups refer to compounds that are prepared by reaction with other compounds.

In several embodiments, one or more compounds of interest can be attached to (A), to (B) or to (A) and (B).

In several embodiments, $R_1$ and $R_2$ independently have the formula:

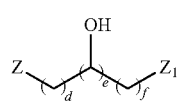
(V)

wherein
d is from 0 to 100
e is from 0 to 100
f is from 0 to 100,
Z is a covalent bond that links one organic moiety to another and in particular to another moiety A or a moiety B as herein defined. and
$Z_1$ is independently selected from —NH$_2$, —OH, —SH, and —COOH In several embodiments, Z can independently be selected from —NH—, —C(=O)NH—, —NH—C(=O), —SS—, —C(=O)O—, —NH(=NH$_2^+$)- or —O—C(=O)—

In several embodiments where the structural unit A of a polymer containing a polyol has formula (IV), X can be $C_vH_{2v+1}$, where v=0-5 and Y can be —OH In some embodiments, R1 and/or R2 have formula (V) where Z is —NH(=NH$_2^+$)— and/or $Z_1$ is NH$_2$.

In several embodiments, in polymers containing a polyol of the particle herein described (A) can be independently selected from the formulas

VI

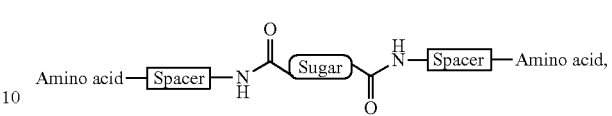
VII

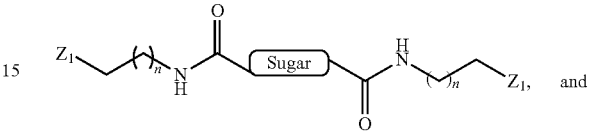
VIII wherein
the spacer is independently selected from any organic moiety, and in particular can include alkyl, phenyl or alkoxy groups optionally containing a heteroatom, such as sulfur, nitrogen, oxygen or fluorine;
the amino acid is selected from any organic group bearing a free amine and a free carboxylic acid group;
n is from 1 to 20; and
$Z_1$ is independently selected from —NH$_2$, —OH, —SH, and —COOH.

In several embodiments, Z1 is NH2, and/or the sugar can be any monosaccharide such as glucose, fructose, mannitol, sucrose, galactose, sorbitol, xylose or galactose.

In several embodiments, in polymers containing a polyol of the particle herein described one ore more structural units (A) can independently have the formula

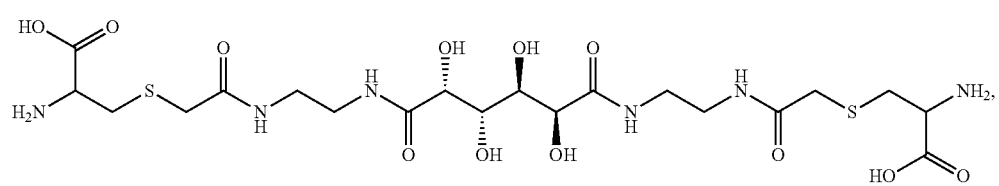
IX

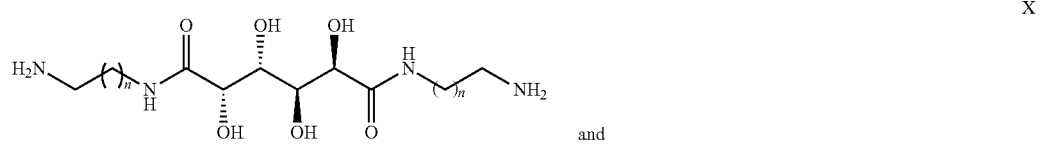
X and

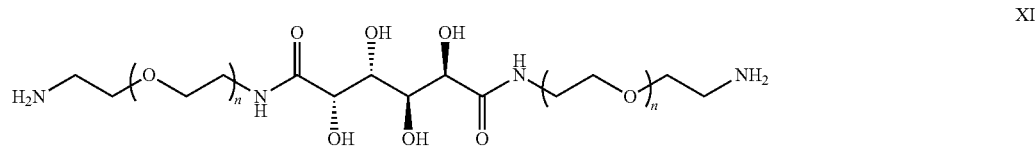
XI

In several embodiments, (B) can be formed by any straight, branched, symmetric or asymmetric compound linking the two (A) moieties through functional groups.

In several embodiments, (B) can be formed by a compound where at least two cross-linkable groups linking the two (A) moieties.

In some embodiments, (B) contains a neutral, cationic or anionic organic group whose nature and composition is dependent on the chemical nature of the compound to be covalently or non-covalently tethered Exemplary cationic moieties of (B) for use with anionic cargo include, but are not limited to, organic groups bearing amidines groups, quartenary ammoniums, primary amine group, secondary amine group, tertiary amine groups (protonated below their pKa's), and immidazoliums Exemplary anionic moieties contained in (B) for use with cationic cargo include, but are not limited to, organic groups bearing sulfonates of formula, nitrates of formula, carboxylates of formula, and phosphonates In particular one or more cationic or anionic moieties (B) for use with anionic cargo and cationic cargos respectively can independently have a general formula of:

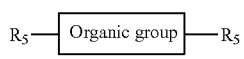
(XII)

wherein $R_5$ is an electrophilic group that can be covalently linked to A when A contains nucleophilic groups. Examples of $R_5$ in this case include but are not limited to —C(=O)OH, —C(=O)Cl, —C(=O)NHS, —C(=NH$_2^+$)OMe, —S(=O)OCl—, —CH$_2$Br, alkyl and aromatic esters, terminal alkynes, tosylate, and mesylate amongst several others. In the case where moiety A contains electrophilic end groups, $R_5$ will bear nucleophilic groups such as —NH$_2$ (primary amines), —OH, —SH, N$_3$ and secondary amines.

In particular, when moiety (B) is a cationic moiety (B) for use with anionic cargo the "organic group" is an organic moiety that can have a backbone with a general formula consisting of $C_mH_{2m}$ with m>1 and other heteroatoms and must contain at least one of the following functional groups including amidines of formula (XIII), quartenary ammoniums of formula (XIV), primary amine group of formula (XV), secondary amine group of formula (XVI), tertiary amine groups of formula (XVII) (protonated below their pKa's), and immidazoliums of formula (XVIII)

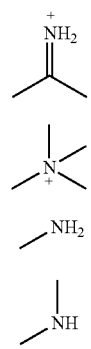

(XIII)

(XIV)

(XV)

(XVI)

(XVII)

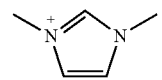
(XVIII)

In embodiments, when moiety (B) is an anionic moiety (B) for use with cationic cargo, the "organic group" may have a backbone with a general formula consisting of $C_mH_{2m}$ with m>1 and other heteroatoms and must contain at least one of the following functional groups including sulfonates of formula (XIX), nitrates of formula (XX), carboxylates of formula (XXI), and phosphonates of formula (XXII)

(XIX)

(XX)

(XXI)

(XXII)

In embodiments wherein (B) is comprised by carboxylates (XXI), a compound containing primary amine or hydroxyl groups can also be attached via the formation of a peptide or an ester bond.

In embodiments wherein (B) is comprised of primary amine group of formula (XV), and/or secondary amine group of formula (XVI), a compound containing carboxylic acid groups can also be attached via the formation of a peptide bond.

In several embodiments moiety (B) can independently be selected from

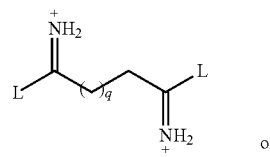
(XXIII)

or

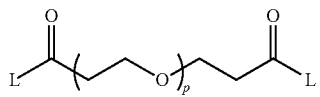
(XXIV)

in which
q is from 1 to 20; and in particular can be 5
p is from 20 to 200; and

L is a leaving group.

The term "leaving group" as used herein indicates a molecular fragment that departs with a pair of electrons in heterolytic bond cleavage. In particular, a leaving group can be anions or neutral molecules, and the ability of a leaving group to depart is correlated with the $pK_a$ of the conjugate acid, with lower $pK_a$ being associated with better leaving group ability. Exemplary anionic leaving groups include halides such as $Cl^-$, $Br^-$, and $I^-$, and sulfonate esters, such as para-toluenesulfonate or "tosylate" ($TsO^-$). Exemplary neutral molecule leaving groups are water ($H_2O$), ammonia ($NH_3$), and alcohols (ROH).

In particular, in several embodiments, L can be a chloride (Cl), methoxy (OMe), t butoxy (OtBU) or N hydrosuccinimide (NHS).

In some embodiments the structural unit of formula (I) can have formula

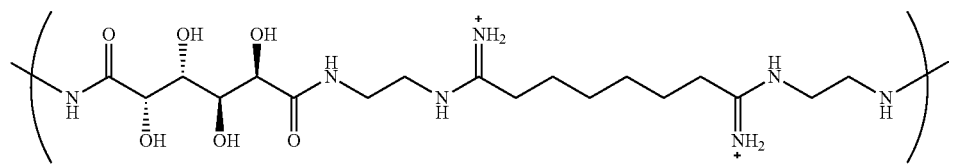
(XXV)

In some embodiments the structural unit of formula (II) can have formula

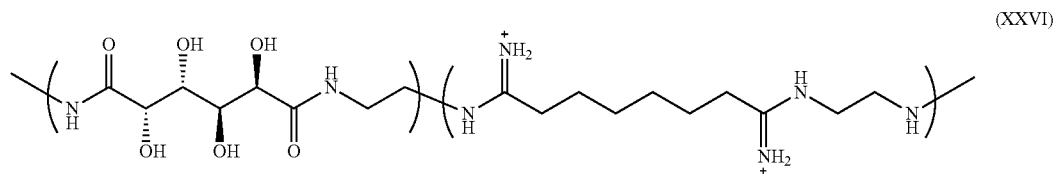
(XXVI)

In some embodiments the structural unit of formula (III) can have formula

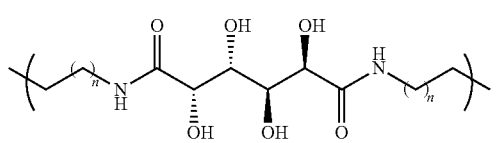
(XXVII)

or

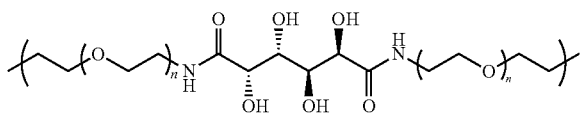
(XXVIII)

in which n is from 1 to 20 and in particular from 1 to 4.

In some embodiments, the polymer containing polyol can have the formula

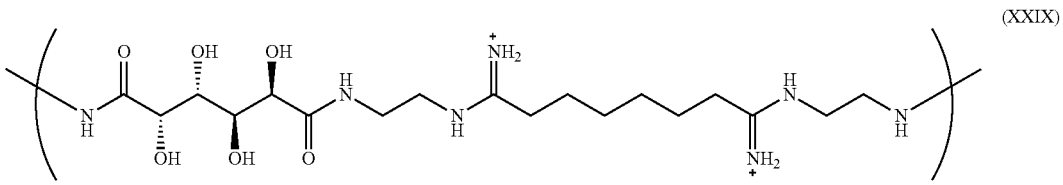
(XXIX)

In some embodiments, the polymer containing a boronic acid contains at least one terminal boronic acid group and has the following structure:

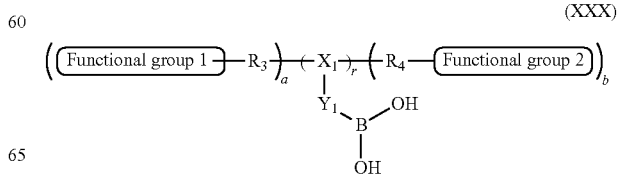
(XXX)

wherein

R₃ and R₄ can be independently selected from any hydrophilic organic polymer, and in particular can independently be any poly(ethylene oxides), and zwitterionic polymers.

X₁ can be an organic moiety containing one or more of —CH, —N, or —B

Y₁ can be an alkyl group with a formula —$C_mH_{2m}$— with m>1, possibly containing olefins or alkynyl groups, or an aromatic group such as a phenyl, biphenyl, napthyl or anthracenyl r is from 1 to 1000, a is from 0 to 3, and b is from 0 to 3 and wherein functional group 1 and functional group 2 are the same or different and are able to bind to a targeting ligand, and in particular a protein, antibody or peptide, or is an end group such as —OH, —OCH₃ or —(X₁)—(Y₁)—B(OH)₂—

In some embodiments, R₃ and R₄ are (CH₂CH₂O)ₜ, where t is from 2 to 2000 and in particular from 100 to 300

In some embodiments X₁ can be —NH—C(=O)—, —S—S—, —C(=O)—NH—, —O—C(=O)— or —C(=O)—O— and/or Y₁ can be a phenyl group.

In some embodiments r can be 1, a can be 0 and b can be 1.

In some embodiments, functional group 1 and functional group 2 are the same or different and are independently selected from. —B(OH)₂, —OCH₃, —OH.

In particular, functional group 1 and/or 2 of formula (XXXI) can be a functional group able to bind a cargo and in particular a targeting ligand such as a protein, antibody or peptide, or can be an end group such as —OH, —OCH₃ or —(X)—(Y)—B(OH)₂.

The term "functional group" as used herein indicates specific groups of atoms within a molecular structure or portion thereof that are responsible for the characteristic chemical reactions of that structure or portion thereof. Exemplary functional groups include hydrocarbons, groups containing halogen, groups containing oxygen, groups containing nitrogen and groups containing phosphorus and sulfur all identifiable by a skilled person. In particular, functional groups in the sense of the present disclosure include a carboxylic acid, amine, triarylphosphine, azide, acetylene, sulfonyl azide, thio acid and aldehyde. In particular, for example, a functional group able to bind a corresponding functional group in a targeting ligand can be selected to comprise the following binding partners: carboxylic acid group and amine group, azide and acetylene groups, azide and triarylphosphine group, sulfonyl azide and thio acid, and aldehyde and primary amine. Additional functional groups can be identified by a skilled person upon reading of the present disclosure. As used herein, the term "corresponding functional group" refers to a functional group that can react to another functional group. Thus, functional groups that can react with each other can be referred to as corresponding functional groups.

An end-group indicates a constitutional unit that is an extremity of a macromolecule or oligomer molecule. For example the end-group of a PET polyester may be an alcohol group or a carboxylic acid group. End groups can be used to determine molar mass. Exemplary end groups comprise —OH. —COOH, NH₂, and OCH₃, In some embodiments, the polymer containing boronic acid can have formula

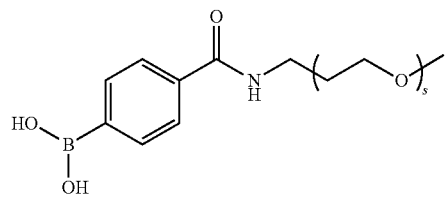

(XXXI)

wherein s is from 20 to 300.

Exemplary agents and targeting ligands that can be attached to nanoparticles of the present disclosure comprise organic or inorganic molecules, including polynucleotides, nucleotides, aptamers polypeptides, proteins, polysaccharides macromolecular complexes including but not limited to those comprising a mixture of protein and polynucleotides, saccharides and/or polysaccharides, viruses, molecules with radioisotopes, antibodies or antibody fragments.

The term "polynucleotide" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base and to a phosphate group and that is the basic structural unit of nucleic acids. The term "nucleoside" refers to a compound (such as guanosine or adenosine) that consists of a purine or pyrimidine base combined with deoxyribose or ribose and is found especially in nucleic acids. The term "nucleotide analog" or "nucleoside analog" refers respectively to a nucleotide or nucleoside in which one or more individual atoms have been replaced with a different atom or a with a different functional group. Accordingly, the term "polynucleotide" includes nucleic acids of any length, and in particular DNA, RNA, analogs and fragments thereof. A polynucleotide of three or more nucleotides is also called "nucleotidic oligomer" or "oligonucleotide."

The term "aptamers" as used here indicates oligonucleic acid or peptide molecules that bind a specific target. In particular, nucleic acid aptamers can comprise, for example, nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers are useful in biotechnological and therapeutic applications as they offer molecular recognition properties that rival that of the antibodies Peptide aptamers are peptides that are designed to specifically bind to and interfere with protein-protein interactions inside cells. In particular, peptide aptamers can be derived, for example, according to a selection strategy that is derived from the yeast two-hybrid (Y2H) system. In particular, according to this strategy, a variable peptide aptamer loop attached to a transcription factor binding domain is screened against the target protein attached to a transcription factor activating domain. In vivo binding of the peptide aptamer to its target via this selection strategy is detected as expression of a downstream yeast marker gene.

The term "polypeptide" as used herein indicates an organic linear, circular, or branched polymer composed of two or more amino acid monomers and/or analogs thereof. The term "polypeptide" includes amino acid polymers of any length including full length proteins and peptides, as well as analogs and fragments thereof. A polypeptide of three or more amino acids is also called a protein oligomer, peptide or oligopeptide. In particular, the terms "peptide" and "oligopeptide"

usually indicate a polypeptide with less than 50 amino acid monomers. As used herein the term "amino acid", "amino acidic monomer", or "amino acid residue" refers to any of the twenty naturally occurring amino acids, non-natural amino acids, and artificial amino acids and includes both D an L optical isomers. In particular, non-natural amino acids include D-stereoisomers of naturally occurring amino acids (these including useful ligand building blocks because they are not susceptible to enzymatic degradation). The term "artificial amino acids" indicate molecules that can be readily coupled together using standard amino acid coupling chemistry, but with molecular structures that do not resemble the naturally occurring amino acids. The term "amino acid analog" refers to an amino acid in which one or more individual atoms have been replaced, either with a different atom, isotope, or with a different functional group but is otherwise identical to original amino acid from which the analog is derived. All of these amino acids can be synthetically incorporated into a peptide or polypeptide using standard amino acid coupling chemistries. The term "polypeptide" as used herein includes polymers comprising one or more monomer, or building blocks other than an amino acid monomer. The terms monomer, subunit, or building blocks indicate chemical compounds that under appropriate conditions can become chemically bonded to another monomer of the same or different chemical nature to form a polymer. The term "polypeptide" is further intended to comprise a polymer wherein one or more of the building blocks is covalently bound to another by a chemical bond other than amide or peptide bond.

The term "protein" as used herein indicates a polypeptide with a particular secondary and tertiary structure that can participate in, but not limited to, interactions with other biomolecules including other proteins, DNA, RNA, lipids, metabolites, hormones, chemokines, and small molecules. Exemplary proteins herein described are antibodies.

The term "antibody" as used herein refers to a protein of the kind that is produced by activated B cells after stimulation by an antigen and can bind specifically to the antigen promoting an immune response in biological systems. Full antibodies typically consist of four subunits including two heavy chains and two light chains. The term antibody includes natural and synthetic antibodies, including but not limited to monoclonal antibodies, polyclonal antibodies or fragments thereof. Exemplary antibodies include IgA, IgD, IgG1, IgG2, IgG3, IgM and the like. Exemplary fragments include Fab Fv, Fab' F(ab')2 and the like. A monoclonal antibody is an antibody that specifically binds to and is thereby defined as complementary to a single particular spatial and polar organization of another biomolecule which is termed an "epitope". In some forms, monoclonal antibodies can also have the same structure. A polyclonal antibody refers to a mixture of different monoclonal antibodies. In some forms, polyclonal antibodies can be a mixture of monoclonal antibodies where at least two of the monoclonal antibodies binding to a different antigenic epitope. The different antigenic epitopes can be on the same target, different targets, or a combination. Antibodies can be prepared by techniques that are well known in the art, such as immunization of a host and collection of sera (polyclonal) or by preparing continuous hybridoma cell lines and collecting the secreted protein (monoclonal).

Figure 2:
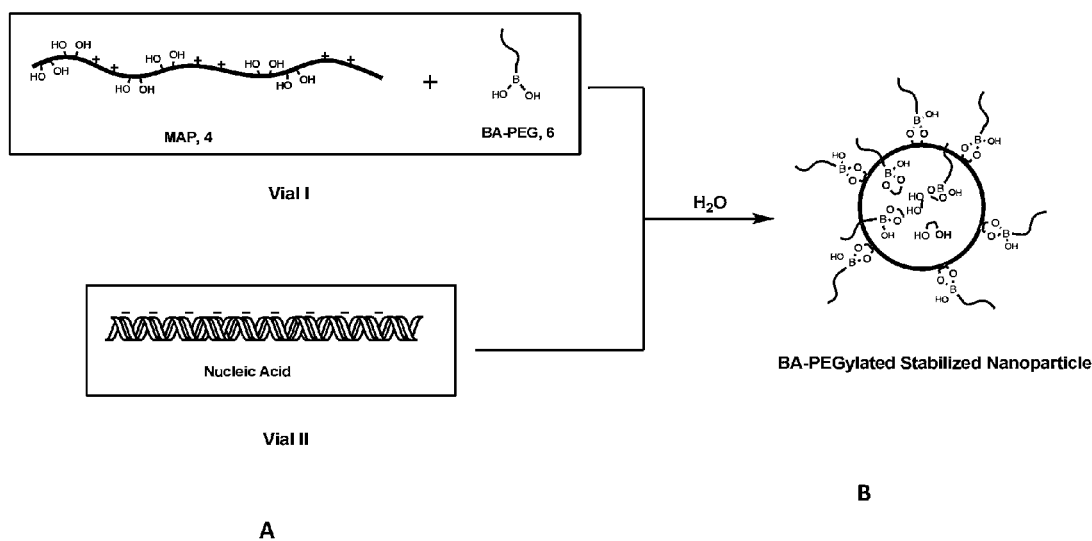
FIG. 2 shows a schematic representation of a nanoparticle and a related method of manufacturing according to an embodiment of the present disclosure. Panel A shows a polymer containing a polyol (MAP, 4) and a polymer containing a boronic acid (BA-PEG, 6) together with a molecule of interest (nucleic acid) according to an embodiment of the present disclosure. Panel B shows a BA-pegylated stabilized nanoparticle formed upon assembly of the polymers and compound shown in panel A.

In several embodiments, polyol polymers form a non-covalent complex or linkage with one or more compounds of interest to be delivered according to the schematic illustration of FIGS. 1 and 2.

In several embodiments, a nanoparticle structure comprises an agent and a polymer containing a polyol, where the agent is linked to a polyol polymer by a covalent bond. An example of a polyol polymer conjugated to an agent is detailed in Examples 16-21. In these embodiments, polyol polymers conjugated to an agent (herein referred to as "polyol polymer-agent conjugate") form nanoparticles whose structure presents sites on their surface for interaction with BA molecules.

In several of those embodiments, the nanoparticle further comprises BA polymers configured to provide steric stabilization and/or targeting functionality to the nanoparticle. In particular, in those embodiments the addition of a BA polymer allows minimizing of self-aggregation and undesired interactions with other nanoparticles, thus providing enhanced salt and serum stability. For example, steric stabilization is herein provided by the BA polymer having PEG as illustrated by the exemplary nanoparticle described in Example 12.

In such embodiments, the structure of this nanoparticle affords several advantages over agents delivery methods of the prior art, such as the ability to provide controlled release of one or more agents. This feature can be provided, for example, by the use of a biodegradable ester linkage between the agent and the polyol polymer. A person skilled in the art will recognize other potential linkages suitable for this purpose. In these embodiments, another advantage is the ability to provide specific targeting of the agent through the BA polymer moiety.

In several embodiments, BA polymers may comprise a fluorinated boronic acid (Example 7) or a fluorinated cleavable boronic acid (Example 8) capable of being used as an imaging agent in MRI or other similar techniques. Such an imaging agent may be useful for tracking the pharmacokinetics or pharmacodynamics of an agent delivered by the nanoparticle.

In several embodiments, a nanoparticle structure comprises an agent and a polyol polymer, where the nanoparticle is a modified liposome. In these embodiments, the modified liposome comprises lipids conjugated to polyol polymers via a covalent linkage such that the surface of the liposome presents polyol polymers. In these embodiments, the modified liposomes form such that the agents to be delivered are contained within the liposome nanoparticle.

The term "liposome" as used herein indicates a vesicular structure comprised of lipids. The lipids typically have a tail group comprising a long hydrocarbon chain and a hydrophilic head group. The lipids are arranged to form a lipid bilayer with an inner aqueous environment suitable to contain an agent to be delivered. Such liposomes present an outer surface that may comprise suitable targeting ligands or molecules for specific recognition by cell surface receptors or other targets of interest.

The term "conjugated" as used herein indicates that one molecule has formed a covalent bond with a second molecule and includes linkages where atoms covalently bond with alternating single and multiple (e.g. double) bonds (e.g., C=C—C=C—C) and influence each other to produce electron delocalization.

In yet other embodiments of the present disclosure, a nanoparticle structure comprises an agent and a polyol, where the nanoparticle is a modified micelle. In these embodiments, the modified micelle comprises polyol polymers modified to contain a hydrophobic polymer block.

The term "hydrophobic polymer block" as used in the present disclosure indicates a segment of the polymer that on its own would be hydrophobic.

The term "micelle" as used herein refers to an aggregate of molecules dispersed in a liquid. A typical micelle in aqueous solution forms an aggregate with the hydrophilic "head"

regions in contact with surrounding solvent, sequestering the hydrophobic single tail regions in the micelle centre. In the present disclosure the head region may be, for example, a surface region of the polyol polymer while the tail region may be, for example, the hydrophobic polymer block region of the polyol polymer.

In these embodiments, polyol polymers with a hydrophobic polymer block, when mixed with an agent to be delivered, arrange to form a nanoparticle that is a modified micelle with agents to be delivered contained within the nanoparticle. Such nanoparticle embodiments present polyol polymers on their surface that are suitable to interact with BA polymers that do or do not have targeting functionality according to previous embodiments. In these embodiments, BA polymers capable of use for this purpose include those with hydrophilic A and hydrophobic B in formula (I) or (II). This interaction provides the same or similar advantages as it does for other nanoparticle embodiments mentioned above.

In some embodiments, nanoparticles or related components can be comprised in a composition together with an acceptable vehicle. The term "vehicle" as used herein indicates any of various media acting usually as solvents, carriers, binders, excipients or diluents for a nanoparticle comprised in the composition as an active ingredient.

In some embodiments, where the composition is to be administered to an individual the composition can be a pharmaceutical composition and the acceptable vehicle can be a pharmaceutically acceptable vehicle.

In some embodiments, a nanoparticle can be included in pharmaceutical compositions together with an excipient or diluent. In particular, in some embodiments, pharmaceutical compositions are disclosed which contain nanoparticle, in combination with one or more compatible and pharmaceutically acceptable vehicle, and in particular with pharmaceutically acceptable diluents or excipients.

The term "excipient" as used herein indicates an inactive substance used as a carrier for the active ingredients of a medication. Suitable excipients for the pharmaceutical compositions herein disclosed include any substance that enhances the ability of the body of an individual to absorb the nanoparticle. Suitable excipients also include any substance that can be used to bulk up formulations with nanoparticles to allow for convenient and accurate dosage. In addition to their use in the single-dosage quantity, excipients can be used in the manufacturing process to aid in the handling of nanoparticles. Depending on the route of administration, and form of medication, different excipients may be used. Exemplary excipients include but are not limited to antiadherents, binders, coatings disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluents include any substance that can decrease the viscosity of a medicinal preparation.

In certain embodiments, compositions and, in particular, pharmaceutical compositions can be formulated for systemic administration, which includes parenteral administration and more particularly intravenous, intradermic, and intramuscular administration.

Exemplary compositions for parenteral administration include but are not limited to sterile aqueous solutions, injectable solutions or suspensions including nanoparticles. In some embodiments, a composition for parenteral administration can be prepared at the time of use by dissolving a powdered composition, previously prepared in a freeze-dried lyophilized form, in a biologically compatible aqueous liquid (distilled water, physiological solution or other aqueous solution).

The term "lyophilization" (also known as freeze-drying or cryodesiccation) indicates a dehydration process typically used to preserve a perishable material or make the material more convenient for transport. Freeze-drying works by freezing the material and then reducing the surrounding pressure and adding enough heat to allow the frozen water in the material to sublime directly from the solid phase to gas.

In pharmaceutical applications freeze-drying is often used to increase the shelf life of products, such as vaccines and other injectables. By removing the water from the material and sealing the material in a vial, the material can be easily stored, shipped, and later reconstituted to its original form for injection.

In several embodiments nanoparticles herein described are delivered to a predetermined target. In some embodiments, the target is an in vitro biological system and the method comprises contacting target with the nanoparticle herein described.

In some embodiments, a method is provided for delivery of an agent to an individual where the method comprises formulating a suitable nanoparticle according to various disclosed embodiments. The nanoparticles may also be formulated into a pharmaceutically acceptable composition according to several disclosed embodiments. The method further comprises delivering a nanoparticle to a subject. To deliver the nanoparticle to an individual, the nanoparticle or nanoparticle formulations may be given orally, parenterally, topically, or rectally. They are delivered in forms suitable for each administration route. For example, nanoparticle compositions can be administered in tablets or capsule form, by injection, inhalation, eye lotion, ointment, suppository, infusion; topically by lotion or ointment; and rectally by suppositories.

The term "individual" as used herein includes a single biological organism including but not limited to plants or animals and in particular higher animals and in particular vertebrates such as mammals and in particular human beings.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradennal, intraperitoneal, transtracheal, subcutaneous, subcuticular, intraarticular, subcapsular, subarachnoid, intraspinal and intrastemal, injection and infusion.

The phrases "systemic administration," "administered systemically," "peripheral administration" and "administered peripherally" as used herein mean the administration of a nanoparticle or composition thereof other than directly into the central nervous system, such that it enters the individual's system and, thus, is subject to metabolism and other like processes, for example, subcutaneous administration.

Actual dosage levels of the active ingredient or agent in the pharmaceutical compositions herein described may be varied so as to obtain an amount of the active ingredient which is effective to achieve the desired therapeutic response for a particular individual, composition, and mode of administration, without being toxic to the individual.

These therapeutic polymer conjugate may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the therapeutic polymer conjugate, which may be used in a suitable hydrated fonn, and/or the pharmaceutical compositions of the present invention, are formulated into pharmaceutically acceptable dosage forms by conventional methods known to those of skill in the art.

In particular in some embodiments, the compound delivered is a drug for treating or preventing a condition in the individual.

The term "drug" or "therapeutic agent" indicates an active agent that can be used in the treatment, prevention, or diagnosis of a condition in the individual or used to otherwise enhance the individual's physical or mental well-being.

The term "condition" as used herein indicates a usually the physical status of the body of an individual, as a whole or of one or more of its parts, that does not conform to a physical status of the individual, as a whole or of one or more of its parts, that is associated with a state of complete physical, mental and possibly social well-being. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms. Exemplary conditions include but are not limited to injuries, disabilities, disorders (including mental and physical disorders), syndromes, infections, deviant behaviors of the individual and atypical variations of structure and functions of the body of an individual or parts thereof.

The term "treatment" as used herein indicates any activity that is part of a medical care for or deals with a condition medically or surgically.

The term "prevention" as used herein indicates any activity, which reduces the burden of mortality or morbidity from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

Exemplary compounds that can be delivered by the nanoparticles herein described and that are suitable as drugs comprise compounds able to emit electromagnetic radiations (such as $^{10}B$ isotopes) to be used in radiation treatments (such as boron neutron capture) Additional therapeutic agents comprise any lipophilic or hydrophilic, synthetic or naturally occurring biologically active therapeutic agent including those known in the art. The Merck Index, An Encyclopedia of Chemicals, Drugs, and Biologicals, 13th Edition, 2001, Merck and Co., Inc., Whitehouse Station, N.J. Examples of such therapeutic agents include, but are not limited to, small molecule pharmaceuticals, antibiotics, steroids, polynucleotides (e.g. genomic DNA, cDNA, mRNA, siRNA, shRNA, miRNA, antisense oligonucleotides, viruses, and chimeric polynucleotides), plasmids, peptides, peptide fragments, small molecules (e.g. doxorubicin), chelating agents (e.g. deferoxamine (DESFERAL), ethylenediaminetetraacetic acid (EDTA)), natural products (e.g. Taxol, Amphotericin), and other biologically active macromolecules such as, for example, proteins and enzymes. See also U.S. Pat. No. 6,048,736 which lists active agents (therapeutic agents) that can be used as therapeutic agent with nanoparticles herein described. Small molecule therapeutic agents may not only be the therapeutic agent within the composite particle but, in an additional embodiment, may be covalently bound to a polymer in the composite. In several embodiments, the covalent bond is reversible (e.g. through a prodrug form or biodegradable linkage such as a disulfide) and provides another way of delivering the therapeutic agent. In several embodiments therapeutic agent that can be delivered with the nanoparticles herein described include chemotherapeutics such as epothilones, camptothecin-based drugs, taxol, or a nucleic acid such as a plasmid, siRNA, shRNA, miRNA, antisense oligonucleotides aptamers or their combination, and additional drugs identifiable by a skilled person upon reading of the present disclosure.

In some embodiments, the compound delivered is a compound suitable for imaging a cell or tissue of the individual. Exemplary compounds that can be delivered by the nanoparticles herein described and that are suitable for imaging comprise compounds that contain isotopes such as $^{19}F$ isotopes for MR imaging, $^{18}F$ or $^{64}Cu$ for PET imaging etc.

In particular, the nanoparticles described herein can be configured to contain $^{19}F$-containing BA polymers. For example, $^{19}F$ atoms can be incorporated into a non-cleavable or cleavable BA polymer compound. Other locations for the $^{19}F$ atoms are possible on the BA polymer component, the polyol polymer component, or on the agent to be delivered. These and other variations will be apparent to one skilled in the art.

In several embodiments, the nanoparticles herein described can be used to deliver chemicals used in the agricultural industry. In another embodiment of the invention, the agent delivered by the nanoparticle herein described is a biologically active compound having microbiocidal and agricultural utility. These biologically active compounds include those known in the art. For example, suitable agriculturally biologically active compounds include, but are not limited to, fertilizers, fungicides, herbicides, insecticides, and mildewcides. Microbicides are also used in water-treatment to treat municipal water supplies and industrial water systems such as cooling waters, white water systems in papermaking Aqueous systems susceptible to microbiological attack or degradation are also found in the leather industry, the textile industry, and the coating or paint industry. Examples of such microbicides and their uses are described, individually and in combinations, in U.S. Pat. Nos. 5,693,631, 6,034,081, and 6,060,466, which are incorporated herein by reference. Compositions containing active agents such as those discussed above may be used in the same manner as known for the active ingredient itself. Notably, because such uses are not pharmacological uses, the polymer of the composite does not necessarily have to meet the toxicity profile required in pharmaceutical uses.

In certain embodiments, nanoparticles comprising polyol polymers and BA polymers can also be comprised in a system suitable for delivering any of the compounds herein indicated and in particular agents, using a nanoparticle. In some embodiments of the system, nanoparticles are provided with components suitable for preparing the nanoparticles for administration to an individual.

The systems herein disclosed can be provided in the form of kits of parts. For example the polyol polymers and/or BA polymers can be included as a molecule alone or in the presence of suitable excipients, vehicles or diluents.

In a kit of parts, polyol polymers, BA polymers, and/or agents to be delivered are comprised in the kit independently possibly included in a composition together with suitable vehicle carrier or auxiliary agents. For example, polyol polymers and/or BA polymers can be included in one or more compositions alone and/or included in a suitable vector. Also, an agent to be delivered can be included in a composition together with a suitable vehicle carrier or auxiliary agent. Alternatively, the agent may be supplied by the end user and may be absent from the kit of parts. Furthermore, the polyol polymers, BA polymers and/or agents can be included in various forms suitable for appropriate incorporation into a nanoparticle.

Additional components can also be included and comprise microfluidic chip, reference standards, buffers, and additional components identifiable by a skilled person upon reading of the present disclosure.

In the kit of parts herein disclosed, the components of the kit can be provided, with suitable instructions and other necessary reagents, in order to perform the methods here disclosed. In some embodiments, the kit can contain the compositions in separate containers. Instructions, for example written or audio instructions, on paper or electronic support such as tapes or CD-ROMs, for carrying out the assay, can also be included in the kit. The kit can also contain, depending on the particular method used, other packaged reagents and materials (such as wash buffers and the like).

Further details concerning the identification of the suitable carrier agent or auxiliary agent of the compositions, and generally manufacturing and packaging of the kit, can be identified by the person skilled in the art upon reading of the present disclosure.

In some embodiments, a nanoparticle may be prepared by preparing the individual components of the nanoparticle followed by mixing the components in various orders to arrive at a desired composite nanoparticle structure. Preparation and mixing of components is carried out in suitable solutions known by those skilled in the art.

The term "mixing" as used herein indicates addition of one solution comprising a molecule of interest with another solution comprising another molecule of interest. For example, an aqueous solution of polyol polymers may be mixed with an aqueous solution of BA polymers in the context of the present disclosure.

The term "solution" as used herein indicates any liquid phase sample containing molecules of interest. For example, an aqueous solution of polyol polymers may comprise polyol polymers diluted in water or any buffered solution, in particular aqueous solutions.

In some embodiments, a nanoparticle can be prepared by mixing polyol polymers with an agent to be delivered (FIGS. 1 and 2), forming a polyol polymer-agent nanoparticle. In other embodiments, a nanoparticle may be prepared by further mixing BA polymers with the polyol polymer-agent nanoparticle. In other embodiments, a nanoparticle is prepared by mixing polyol polymers with BA polymers, followed by mixing an agent to be delivered. In yet other embodiments, a nanoparticle is prepared by simultaneously mixing polyol polymers, BA polymers, and an agent to be delivered.

In some embodiments, a nanoparticle is prepared by forming a polyol polymer-agent conjugate according to various embodiments of the present disclosure, thus preparing a nanoparticle comprised of a polyol polymer-agent conjugate. In other embodiments nanoparticles comprised of a polyol polymer-agent conjugates may be prepared by dissolving the nanoparticles in a suitable aqueous solution. In yet further embodiments, nanoparticles comprised of a polyol polymer-agent conjugates may be prepared by mixing polyol polymer-agent conjugates with BA polymers that do or do not provide targeting ligand.

In some embodiments, a nanoparticle can be prepared by mixing polyol polymers with a hydrophobic polymer block with an agent to be delivered, thus preparing a modified micelle according to embodiments of the present disclosure. In other embodiments, a nanoparticle may be prepared by further mixing the modified micelle with BA polymers. In yet other embodiments, a nanoparticle may be prepared by mixing polyol polymers with BA polymers, followed by mixing an agent to be delivered, thus preparing a nanoparticle that is a modified micelle.

In some embodiments of the present disclosure, a nanoparticle can be prepared by mixing lipids conjugated with polyol polymers with BA polymers and/or agents to be delivered, thus preparing a modified liposome. In various embodiments, a nanoparticle may be prepared by mixing lipids conjugated with polyol polymers with BA polymers, followed by mixing agents to be delivered. In other embodiments, a nanoparticle may be prepared by mixing lipids conjugated with polyol polymers with agents to be delivered. In other embodiments, a nanoparticle may be prepared by mixing lipids conjugated with polyol polymers with agents to be delivered, followed by mixing BA polymers, thus preparing a nanoparticle that is a modified liposome.

The formation of nanoparticles according to several embodiments of the present disclosure can be analyzed with techniques and procedures known by those with skill in the art. For example, in several embodiments, gel retardation assays are used to monitor and measure the incorporation of a nucleic acid agent within a nanoparticle (Example 10). In several embodiments, a suitable nanoparticle size and/or zeta potential can be chosen using known methods (Example 11).

Further details concerning the identification of the suitable carrier agent or auxiliary agent of the compositions, and generally manufacturing and packaging of the kit, can be identified by the person skilled in the art upon reading of the present disclosure.

EXAMPLES

The methods system herein described are further illustrated in the following examples, which are provided by way of illustration and are not intended to be limiting. A person skilled in the art will appreciate the applicability of the features described in detail for methods of nucleic acid detection and detection of other targets, such as proteins, antigens, eukaryotic or prokaryotic cells, and the like.

All chemical reagents were obtained from commercial suppliers and were used as received without further purification. Polymer samples were analyzed on a Viscotek GPC System equipped with a TDA 302 triple detector array consisting of a differential refractive index (RI) detector, a differential viscometer and a low angle light scattering detector. A 7.5% acetic acid solution was used as eluant at a 1 mL/min flow rate.

pGL3, a plasmid containing the firefly luciferase gene was extracted and purified from bacteria expressing pGL3. siGL3 was purchased from Integrated DNA Technologies (sequence provided below). siCON1 (sequence provided below) was purchased from Dharmacon. HeLa cells were used to determine the efficacy of pDNA or siRNA delivery by the cationic mucic acid diamine-DMS polymer.

TABLE 1 siRNA sequences

| Plasmid | Sequences | | SEQ ID NO |
|---|---|---|---|
| siGL3 | GUGCCAGAGUCCUUCGAUAdTdT | (sense) | SEQ ID NO: 1 |
|  | UAUCGAAGGACUCUGGCACdTdT | (antisense) | SEQ ID NO: 2 |
| siCON1 | UAGCGACUAAACACAUCAAUU | (sense) | SEQ ID NO: 3 |
|  | UUGAUGUGUUUAGUCGCUAUU | (antisense) | SEQ ID NO: 4 |

Example 1

Synthesis of Mucic Acid Dimethyl Ester, (1)

5 g (22.8 mmol) of mucic acid (Aldrich) was added to a 500 mL round bottom flask containing 120 mL of methanol and 0.4 mL of concentrated sulfuric acid. This mixture was allowed to reflux at 85° C. overnight under constant stirring. The mixture was subsequently filtered, washed with methanol and then recrystallized from a mixture of 80 mL methanol and 0.5 mL triethylamine. After drying under vacuum overnight, 8.0 g (33.6 mmol, 71%) of mucic acid dimethyl ester was obtained. $^1$H NMR ((CD$_3$)$_2$SO) δ 4.88-4.91 (d, 2H), 4.78-4.81 (m, 2H), 4.28-4.31 (d, 2H), 3.77-3.78 (d, 2H), 3.63 (s, 6H). ESI/MS (m/z): 261.0 [M+Na]$^+$

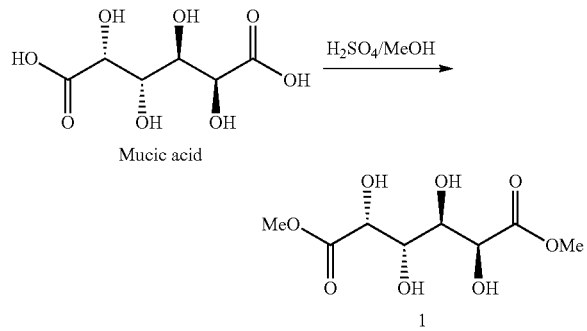

Example 2

Synthesis of N-BOC-Protected Mucic Acid Diamine, (2)

A mixture of 8 g (33.6 mmol) of Mucic Acid Dimethyl Ester (1; Example 1), 12.4 mL (88.6 mmol) triethylamine and 160 mL methanol was heated under reflux at 85° C. in a 500 mL round bottom flask under constant stirring for 0.5 h prior to the addition of 14.2 g (88.6 mmol) N-BOC diamine (Fluka) dissolved in methanol (32 mL). This reaction suspension was then returned to reflux. After refluxing overnight, the mixture was filtered, washed with methanol, recrystallized from methanol and then dried under vacuum to yield 9.4 g (19 mmol, 57%) of N—BOC-Protected Mucic Acid Diamine. $^1$H NMR ((CD$_3$)$_2$SO) δ 7.66 (m, 2H), 6.79 (m, 2H), 5.13-5.15 (d, 2H), 4.35-4.38 (d, 2H), 4.08-4.11 (m, 2H), 3.78-3.80 (d, 2H), 2.95-3.15 (m, 8H), 1.38 (s, 18). ESI/MS (m/z): 517.1 [M+Na]$^+$

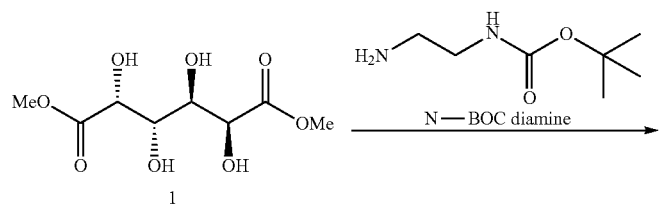

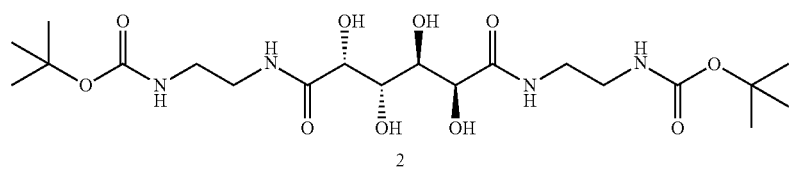

Example 3

Synthesis of Mucic Acid Diamine, (3)

8 g (16.2 mmol) of the N—BOC-Protected Mucic Acid Diamine (2; Example 2) was transferred to a 500 mL round bottom flask containing 3 M HCl in methanol (160 mL) and allowed to reflux overnight at 85° C. under constant stirring. The precipitate was subsequently filtered, washed with methanol and vacuum dried overnight to give 5.7 g (15.6 mmol, 96%) of Mucic Acid Diamine. $^1$H NMR ((CD$_3$)$_2$SO) δ 7.97 (m, 8H), 5.35-5.38 (m, 2H), 4.18-4.20 (m, 2H), 3.82 (m, 2H), 3.35-3.42 (m, 8H), 2.82-2.90 (m, 4H). ESI/MS (m/z): 294.3 [M]$^+$, 317.1 [M+Na]$^+$, 333.0 [M+K]$^+$ texed and centrifuged to dissolve the components. The resulting mixture was stirred at room temperature for 15 h. The mixture was then diluted to 8 mL with water and the pH was brought to 4 with the addition of 1 N HCl. This solution was then dialyzed with a 3500 MWCO dialysis membrane (Pierce pleated dialysis tubing) in ddH$_2$O for 24 h. The dialyzed solution was lyophilized to dryness to give 49 mg of a white fluffy powder. $^1$H NMR (500 MHz, dDMSO) δ 9.15 (bs), 7.92 (bs), 5.43 (bs), 4.58 (bs), 4.17 (bs), 3.82 (bs), 3.37 (bs), 3.28 (bs), 2.82 (bs), 2.41 (bs), 1.61 (bs), 1.28 (bs). $^{13}$C NMR (126 MHz, dDMSO) δ 174.88 (s, 1H), 168.38 (s, 1H), 71.45 (s, 4H), 71.22 (s, 3H), 42.34 (s, 2H), 36.96 (s, 3H), 32.74 (s, 3H), 28.09 (s, 4H), 26.90 (s, 4H). Mw [GPC]=2520, Mw/Mn=1.15.

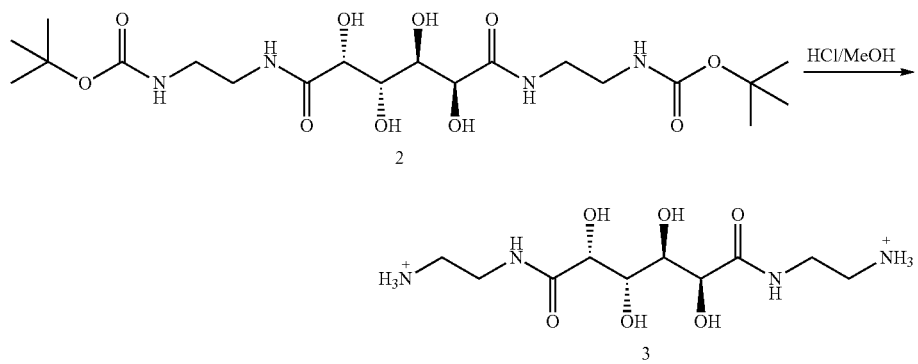

Example 4

Mucic Acid Diamine-DMS Copolymer (MAP), (4)

A 1.5 mL eppendorff tube was charged with a solution of 85.5 mg (0.233 mmol) of the bis(hydrochloride) salt of Example 3 (3) in 0.8 mL of 0.1 M NaHCO$_3$. Dimethylsuberimidate.2HCl (DMS, Pierce Chemical Co., 63.6 mg, 0.233 mmol) was added and the solution was vor-

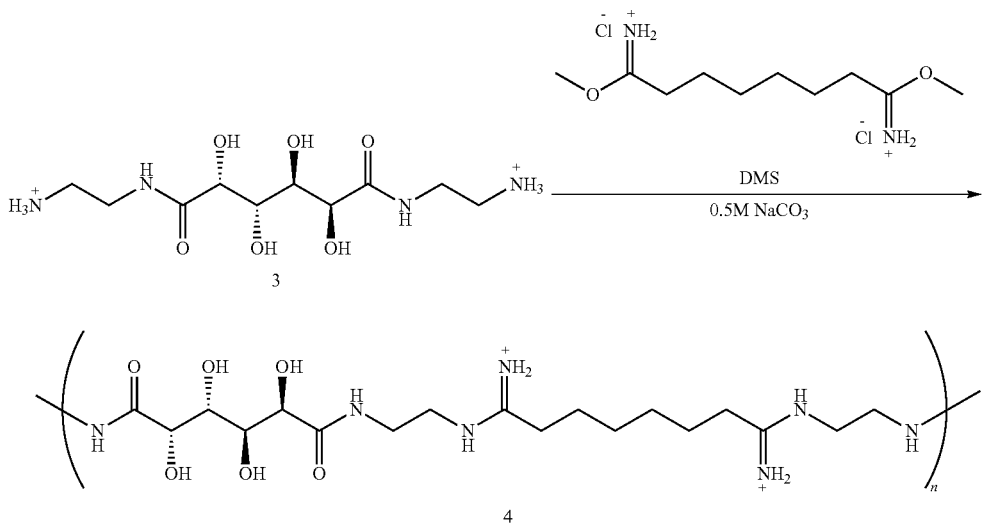

Polymer 4 is an example of a cationic A-B type (repeating structure is ABABAB . . . ) polymer containing a polyol.

Example 5

Boronic Acid-Amide-PEG$_{5000}$, (5)

When a polymer of Example 4 is assembled with nucleic acids, e.g., siRNAs, they will form nanoparticles. These nanoparticles will need to have steric stabilization to be used in mammals and optionally they could have targeting agents included. To perform these two functions, the nanoparticles can be decorated with PEG for steric stabilization and PEG-targeting ligands. To do so, PEG compounds containing boronic acids are prepared. For example, a PEG containing boronic acid can be synthesized according the example below.

332 mg of 4-carboxyphenylboronic acid (2 mmol) was dissolved in 8 mL of SOCl$_2$. To this was added a few drops of DMF and the mixture was refluxed under argon for 2 h. Excess SOCl$_2$ was removed under reduced pressure and the resulting solid was dissolved in 10 mL of anhydrous dichloromethane. To this solution was added 500 mg of PEG$_{5000}$-NH$_2$ (2 mmol) and 418 µL of triethylamine (60 mmol) dissolved in 5 mL of dichloromethane at 0° C. under argon. The resulting mixture was warmed to room temperature and stirring was continued overnight. The dichloromethane solvent was removed under reduced pressure and the resulting liquid was precipitated with 20 mL of diethyl ether. The precipitate was filtered, dried and re-dissolved in ddH$_2$O. The aqueous solution was then filtered with a 0.45 µm filter and dialyzed with a 3500 MWCO dialysis membrane (Pierce pleated dialysis tubing) in ddH$_2$O for 24 h. The dialyzed solution was lyophilized to dryness. $^1$H NMR (300 MHz, dDMSO) δ 7.92-7.77 (m), 4.44 (d), 4.37 (t), 3.49 (m), 2.97 (s).

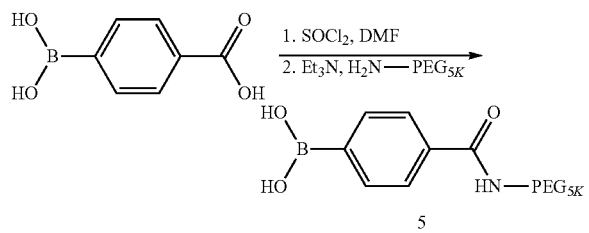

Example 6

Boronic Acid-Disulfide-PEG$_{5000}$, (6)

A cleavable version (under reducing conditions) of the PEG compound of Example 5 can also be synthesized as follows.

250 mg of PEG$_{5000}$-SH (0.05 mmol, LaySanBio Inc.) was added to a glass vial equipped with a stirbar. To this was added 110 mg of aldrithiol-2 (0.5 mmol, Aldrich) dissolved in 4 mL of methanol. The solution was stirred at room temperature for 2 h after which, 77 mg of mercaptophenylboronic acid (0.5 mmol, Aldrich) in 1 mL of methanol was added. The resulting solution was stirred for an additional 2 h at room temperature. Methanol was removed under vacuuo and the residue was re-dissolved in 2 mL of dichloromethane. 18 mL of diethyl ether was added to the dichloromethane solution and the mixture was allowed to sit for 1 h. The resulting precipitate was collected via centrifugation, washed several times with diethyl ether and dried. The dried solid was re-dissolved in water, filtered with a 0.45 µm filter and dialyzed with a 3500 MWCO dialysis membrane (Pierce pleated dialysis tubing) in ddH$_2$O for 15 h. The dialyzed solution was lyophilized to dryness. $^1$H NMR (300 MHz, dDMSO) δ 8.12-8.00 (m), 7.83-7.72 (m), 7.72-7.61 (m), 7.61-7.43 (m), 3.72 (d, J=5.4), 3.68-3.15 (m), 3.01-2.83 (m).

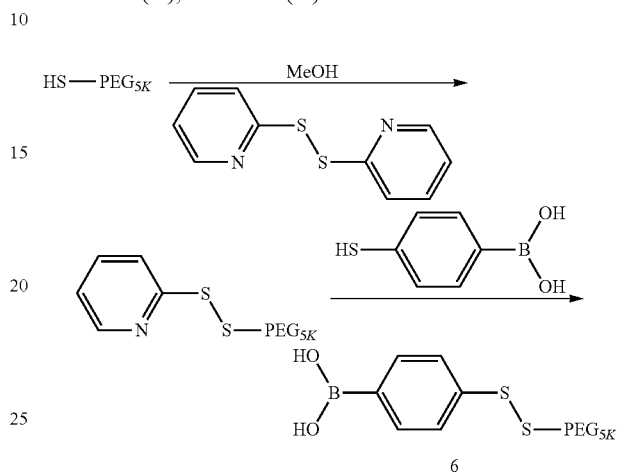

Example 7

Synthesis of (2,3,5,6)-Tetrafluorophenyl Boronic Acid-PEG$_{5000}$, (7)

A fluorinated version of the PEG compound containing boronic acids of Example 5 can be synthesized and used as an imaging agent with the therapeutic nanoparticle. The fluorine atoms for imaging can be incorporated as described and illustrated below.

(2,3,5,6)-fluorocarboxyphenylboronic acid is dissolved in excess SOCl$_2$ (~100 eq.) and to it is added a few drops of DMF. The mixture is refluxed under argon for 2 h. Excess SOCl$_2$ is removed under reduced pressure and the resulting residue is dissolved in anhydrous dichloromethane. To this solution, PEG$_{5000}$-NH$_2$ (1 eq.) and triethylamine (30 eq,) dissolved in dichloromethane is added at 0° C. under argon. The resulting mixture is warmed to room temperature and stirring is continued overnight. The dichloromethane solvent is removed under reduced pressure and the resulting liquid is precipitated with diethyl ether. The precipitate is filtered, dried and re-dissolved in ddH$_2$O. The aqueous solution is then filtered with a 0.45 µm filter and dialyzed with a 3500 MWCO dialysis membrane (Pierce pleated dialysis tubing) in ddH$_2$O for 24 h. The dialyzed solution is lyophilized to dryness.

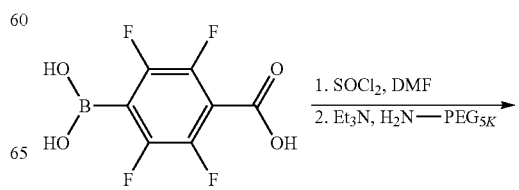

-continued

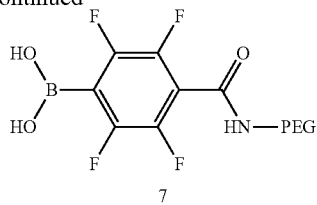

7

The fluorine containing compound is useful to provide $^{19}F$ in the nanoparticle. The $^{19}F$ can be detected by magnetic resonance spectroscopy using a standard patient MRI. The addition of the $^{19}F$ enables the nanoparticles to be imaged (can be done for just imaging or with the addition of a therapeutic agent can allow for imaging and therapy).

Example 8

Synthesis of (2,3,5,6)-Tetrafluorophenyl Boronic Acid-Disulfide-PEG$_{5000}$, (8)

A fluorinated version of the cleavable PEG compound containing boronic acids of Example 5 can be synthesized and used as an imaging agent with the therapeutic nanoparticle. The fluorine atoms for imaging can be incorporated as described and illustrated below.

250 mg of PEG$_{5000}$-SH (0.05 mmol, LaySanBio Inc.) are added to a glass vial equipped with a stirbar. To this is added 110 mg of aldrithiol-2 (0.5 mmol, Aldrich) dissolved in 4 mL of methanol. The solution is stirred at room temperature for 2 h after which, 77 mg of (2,3,5,6)-fluoro-4-mercaptophenyl-boronic acid (0.5 mmol) in 1 mL of methanol is added. The resulting solution is stirred for an additional 2 h at room temperature. Methanol is removed under vacuuo and the residue is re-dissolved in 2 mL of dichloromethane. 18 mL of diethyl ether is added to the dichloromethane solution and the mixture is allowed to sit for 1 h. The resulting precipitate is collected via centrifugation, washed several times with diethyl ether and dried. The dried solid is re-dissolved in water, filtered with a 0.45 μm filter and dialyzed with a 3500 MWCO dialysis membrane (Pierce pleated dialysis tubing) in ddH$_2$O for 15 h. The dialyzed solution is lyophilized to dryness.

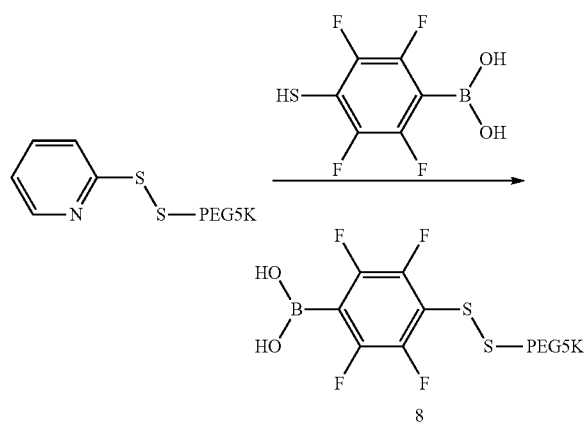

8

Example 9

Synthesis of Boronic Acid-PEG$_{5000}$-Transferrin, (9)

Figure 12:
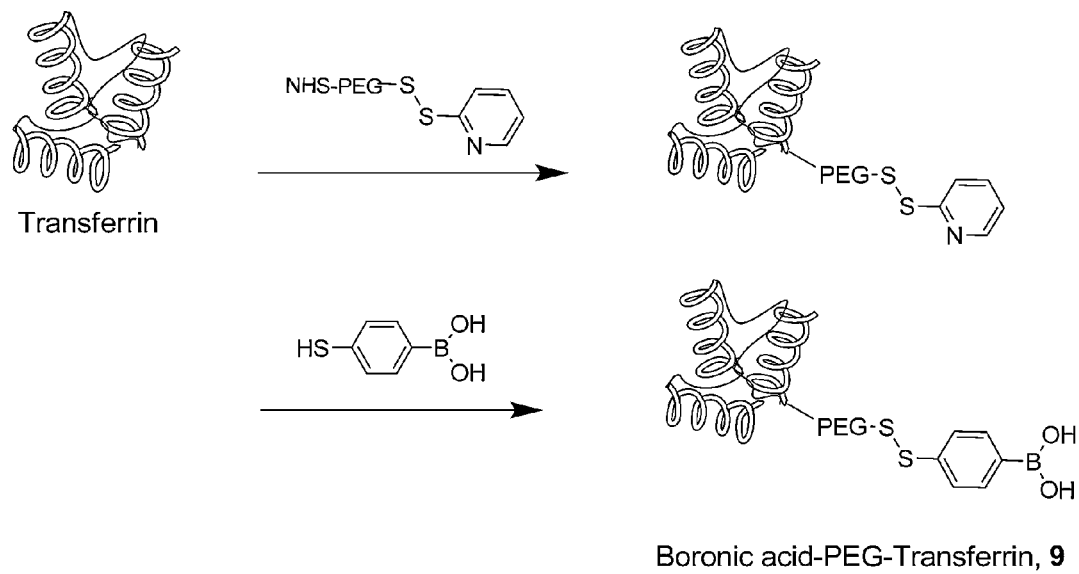
FIG. 12 shows a schematic representation of a synthesis of a polymer containing a boronic acid presenting a targeting ligand according to some embodiments herein described. In particular
Figure 13:
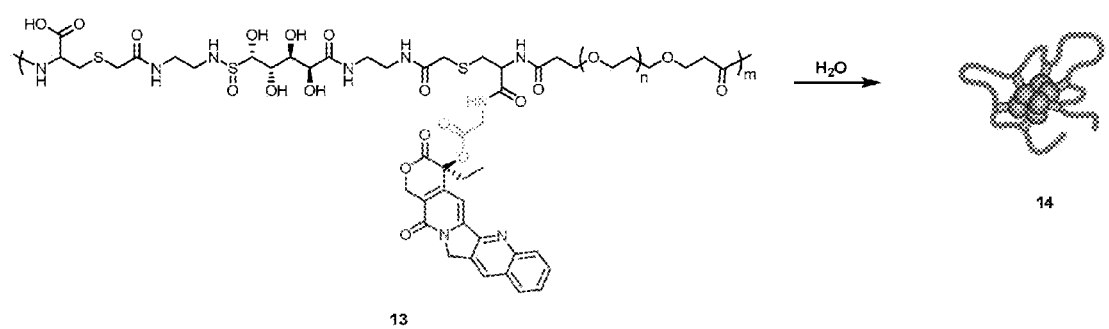
FIG. 13 shows a schematic representation of a synthesis of a nanoparticle according to some embodiments herein described. In particular.
Figure 15:
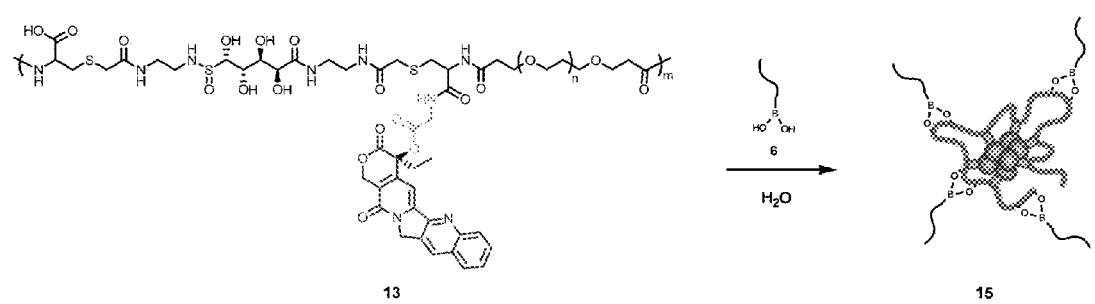
FIG. 15 shows a schematic representation of a synthesis of a nanoparticle according to some embodiments herein described. In particular.

A targeting agent could be placed at the other end of the PEG from the boronic acid in the compounds of Examples 5-8, for example according to an approach schematically illustrated in FIG. 12 with reference to attachment of transferrin.

Thus, the components of a system containing nucleic acids as the therapeutic could be (targeting ligand could be a protein like transferrin (FIG. 12), an antibody or antibody fragment, a peptide like RGD or LHRH, a small molecule like folate or galactose, etc.). A boronic acid PEGylated targeting agent can be synthesized as follows.

In particular, to synthesize the Boronic Acid PEG$_{5000}$-Transferrin according to the approach schematically illustrated in FIG. 12 the following procedure was performed. A solution of 10 mg (0.13 μmol) of Human holo-Transferrin (iron rich) (Sigma Aldrich) in 1 mL of 0.1M PBS buffer (p.H. 7.2) was added to 3.2 mg of OPSS-PEG$_{5000}$-SVA (5 eq, 0.64 μmol, LaysanBio Inc.). The resulting solution was stirred at room temperature for 2 h. The PEGylated Transferrin was purified from the unreacted OPSS-PEG$_{5000}$-SVA using an Ultracel 50,000 MWCO (Amicon Ultra-4, Millipore) and from unreacted Transferrin using a gel filtration column G3000SWx1 (Tosoh Biosep) (confirmed by HPLC and MALDI-TOF analysis). 100 μg of the OPSS-PEG$_{5000}$ PEGylated Transferrin in 100 μL was then incubated at room temperature with 20 μL 4-mercaptophenylboronic acid (1 μg/μL, 20 μg, 100 eq.) for 1 h. After incubation, the solution was dialyzed twice with a YM-30,000 NMWI device (Millipore) to remove excess 4-mercaptophenylboronic and the pyridyl-2-thione by-product.

Example 10

Formulation of MAP-Nucleic Acid Particles—Gel Retardation Assay

Figure 3:
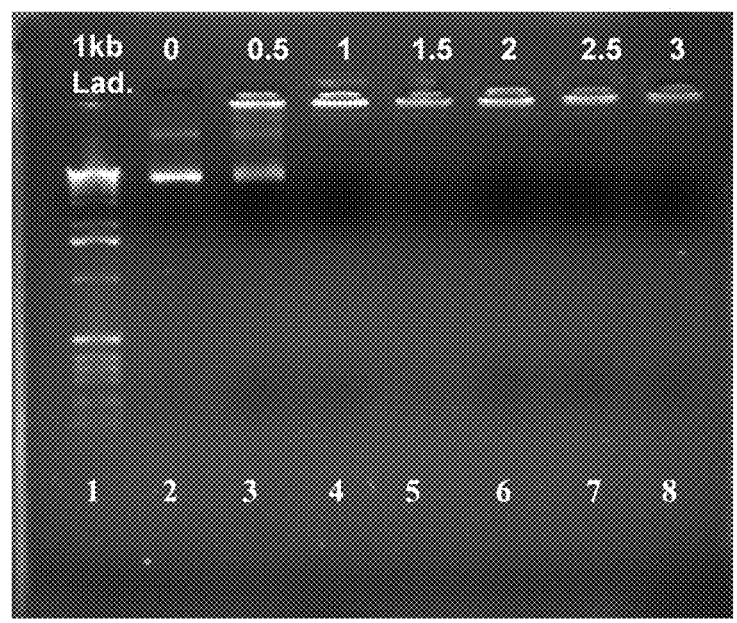
FIG. 3 shows formation of a complex comprising polymers containing polyols and a compound of interest according to an embodiment herein described. In particular.
Figure 4:
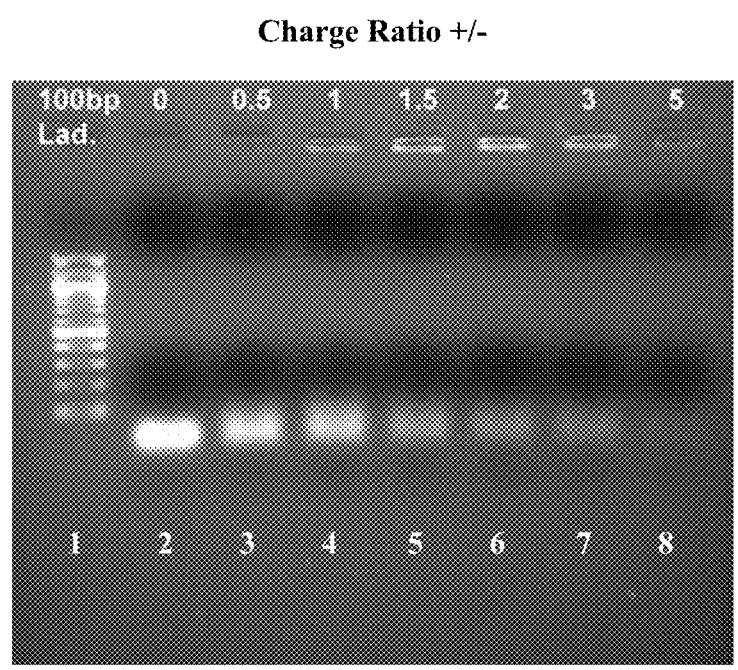
FIG. 4 shows formation of a complex comprising polymers containing polyols and a compound of interest according to an embodiment herein described. In particular.

As diagramed in FIG. 1, 1 μg of plasmid DNA or siRNA in DNAse and RNASe free water (0.1 μg/μL, 10 μL) was mixed with 10 μL of MAP at various concentrations in DNAse and RNASe free water to give charge ratios ("+" charge on polymer to "−" charge on nucleic acid) of 0.5, 1, 1.5, 2, 2.5, and 5. The resulting mixtures were incubated for 30 minutes at room temperature. 10 μL of the 20 μL solutions were loaded onto a 1% agarose gel with 3.5 μL of loading buffer and the gel was electrophoresed at 80 V for 45 minutes as shown in FIGS. 3 and 4. Nucleic acid that is not contained within the nanoparticle will migrate on the gel. These results give guidance to the charge ratios necessary for nucleic acid containment within the nanoparticles.

Example 11

Particle Size and Zeta Potential of MAP-Nucleic Acid Particles

Figure 5:
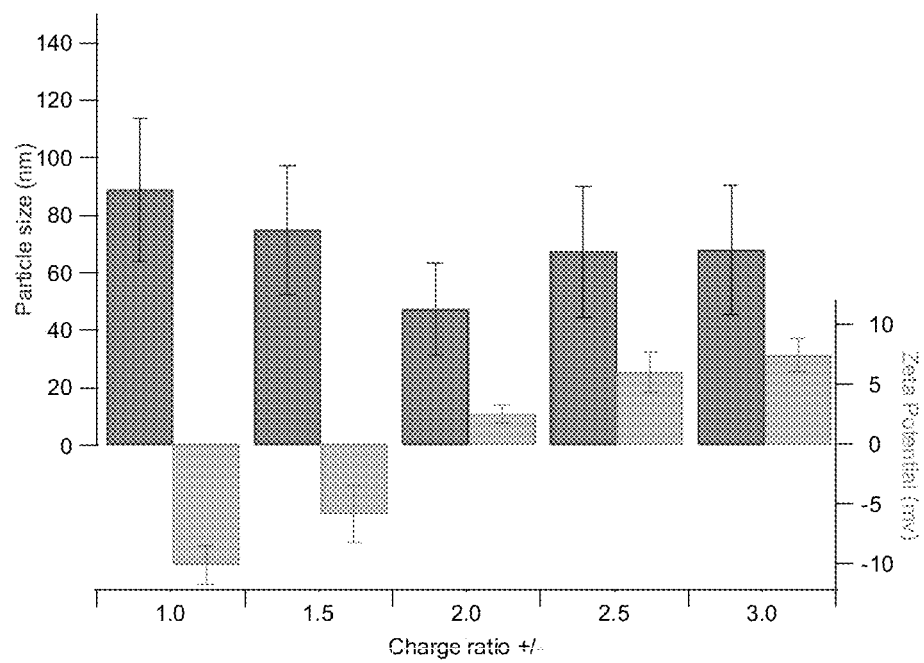
FIG. 5 shows properties of nanoparticles according to some embodiments herein described. In particular.

1 μg of plasmid DNA in DNAse and RNASe free water (0.1 μg/μL, 10 μL) was mixed with 10 μL of MAP at various concentrations in DNAse and RNASe free water to give charge ratios of 0.5, 1, 1.5, 2, 2.5, and 5. The resulting mixtures were incubated for 30 minutes at room temperature. The 20 μL mixture was then diluted with DNAse and RNASe free water to 70 μL for particle size measurements. This 70 μL solution was then diluted to 1400 μL with 1 mM KCl for zeta potential measurements. The particle size and zeta potential measurements were made on a ZetaPals dynamic light scattering (DLS) instrument (Brookhaven Instruments). The results are shown in FIG. 5.

Example 12

Particle Size Stabilization by PEGylation with Boronic Acid $PEG_{5k}$

Figure 6:
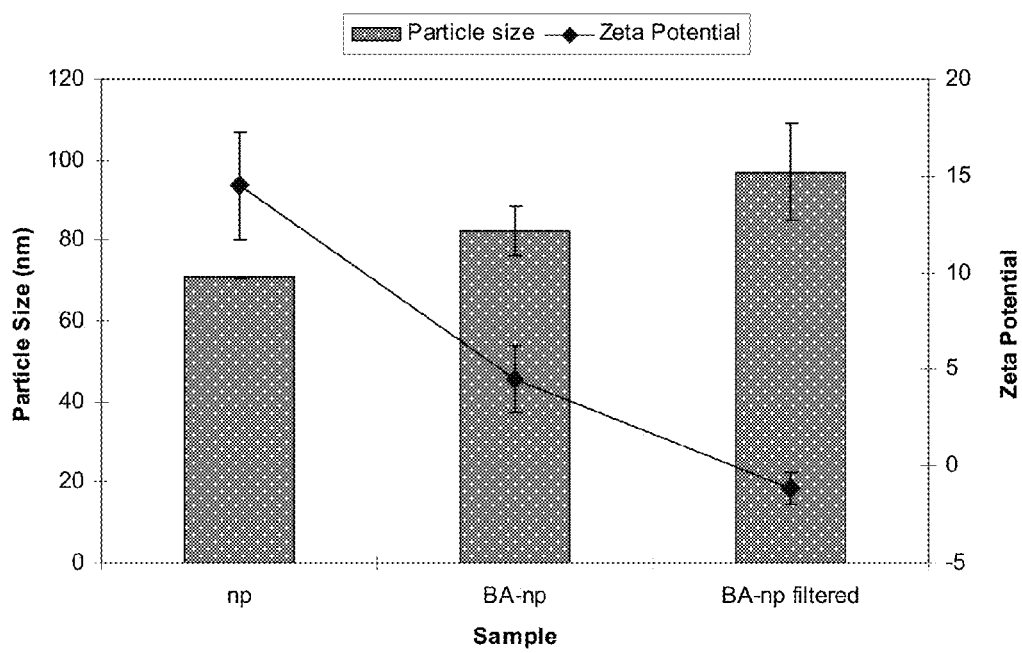
FIG. 6 properties of nanoparticles according to some embodiments herein described. In particular.
Figure 7:
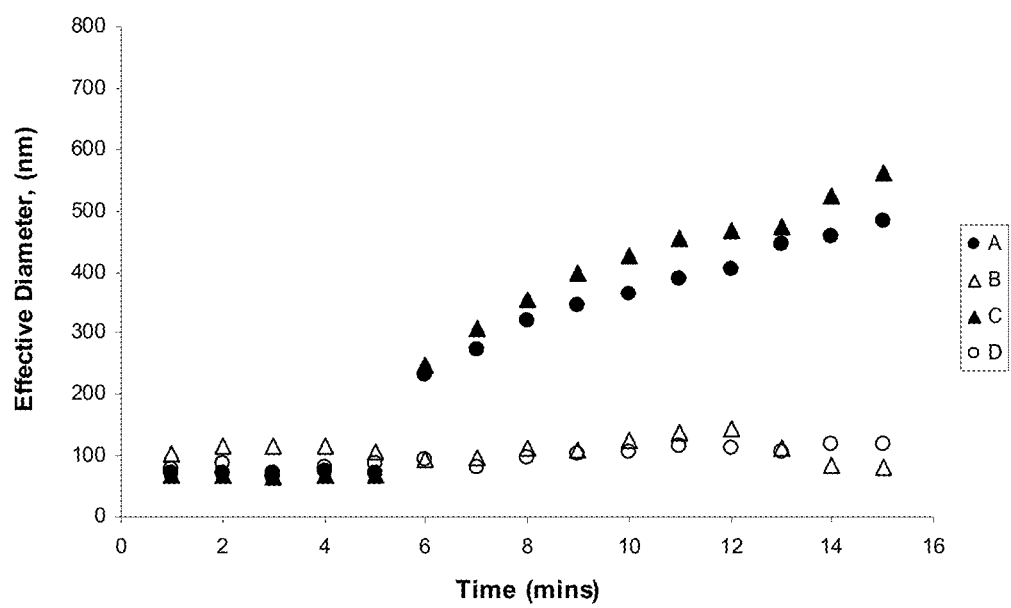
FIG. 7 shows the salt stability of BA-PEGylated MAP-Plasmid Nanoparticles according to an embodiment herein disclosed. Plot A: 5:1 BA-PEG+np+1×PBS after 5 mins; Plot B: 5:1 BA-PEG+np, dialyzed 3× w/100 kDa+1×PBS after 5 mins; Plot C: 5:1 prePEGylated w/BA-PEG+1×PBS after 5 mins; Plot D: 5:1 prePEGylated w/BA-PEG, dialyze 3× w/100 kDa+PBS after 5 mins.

As diagrammed in FIG. 2, 2 µg of plasmid DNA in DNAse and RNASe free water (0.45 µg/µL, 4.4 µL) was diluted to 80 µL in DNAse and RNASe free water. This plasmid solution was mixed with 4.89 µg of MAP (0.5 µg/µL, 9.8 µL) also diluted to 80 µL in DNAse and RNASe free water to give a 3+/− charge ratio and a final plasmid concentration of 0.0125 µg/µL. The resulting mixture was incubated for 30 minutes at room temperature. To this solution was added 480 µg of boronic acid $PEG_{5K}$, (compound 6; Example 6), (20 µg/µL, 24 µL). This mixture was then incubated further for 30 minutes, dialyzed twice in DNAse and RNASe free water with a 0.5 mL 100,000 MWCO membrane (BIOMAX, Millipore Corporation) and reconstituted in 160 µL of DNAse and RNASe free water. Half of the solution was diluted with 1.4 mL of 1 mM KCl for zeta potential measurements (FIG. 6). Note that the zeta potential of the BA containing nanoparticles show a lower zeta potential than the nanoparticles that do not. These results support the conclusion that the BA containing nanoparticles have the BA localized on the exterior of the nanoparticles. The other half was used to measure the particle size. The particle size was measured every minute for 5 minutes after which, 10.2 µL of 10×PBS was added such that the final 90.2 µL solution was in 1×PBS. The particle size was then measured again every minute for another 10 minutes as shown in FIG. 7. The BA containing nanoparticles separated from non-particle components (by filtration) are stable in PBS while the particles without the BA are not. These data support the conclusion that the BA containing nanoparticles have the BA localized on their exterior as they are stabilized against aggregation in PBS.

Example 13

Transfection of MAP/pDNA Particles into HeLa Cells

Figure 8:
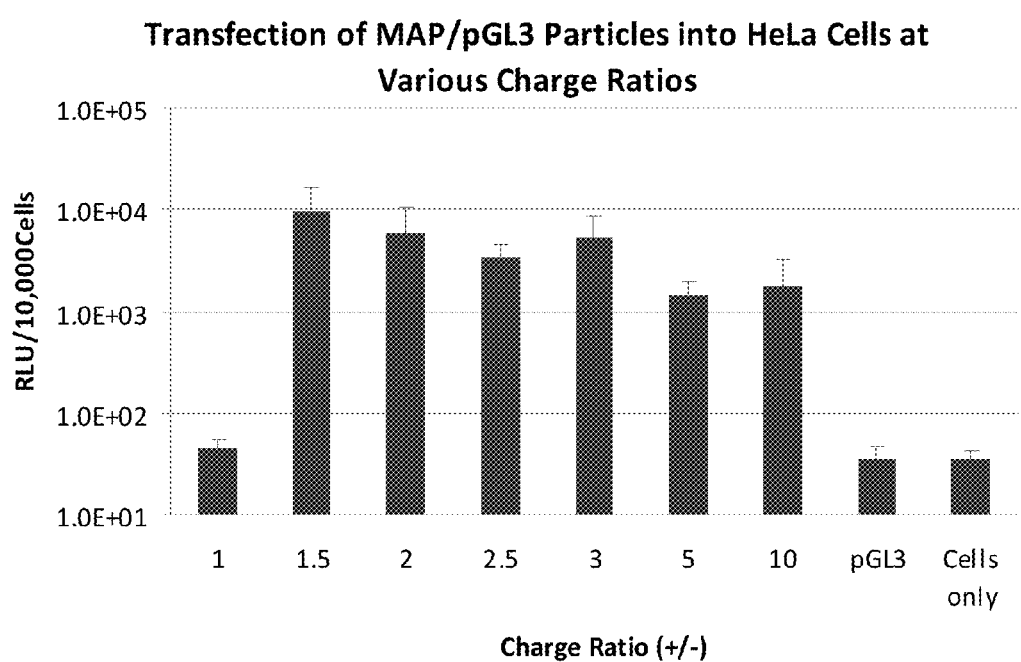
FIG. 8 shows delivery of an agent to human cells in vitro with nanoparticles according to an embodiment herein described. In particular.
Figure 9:
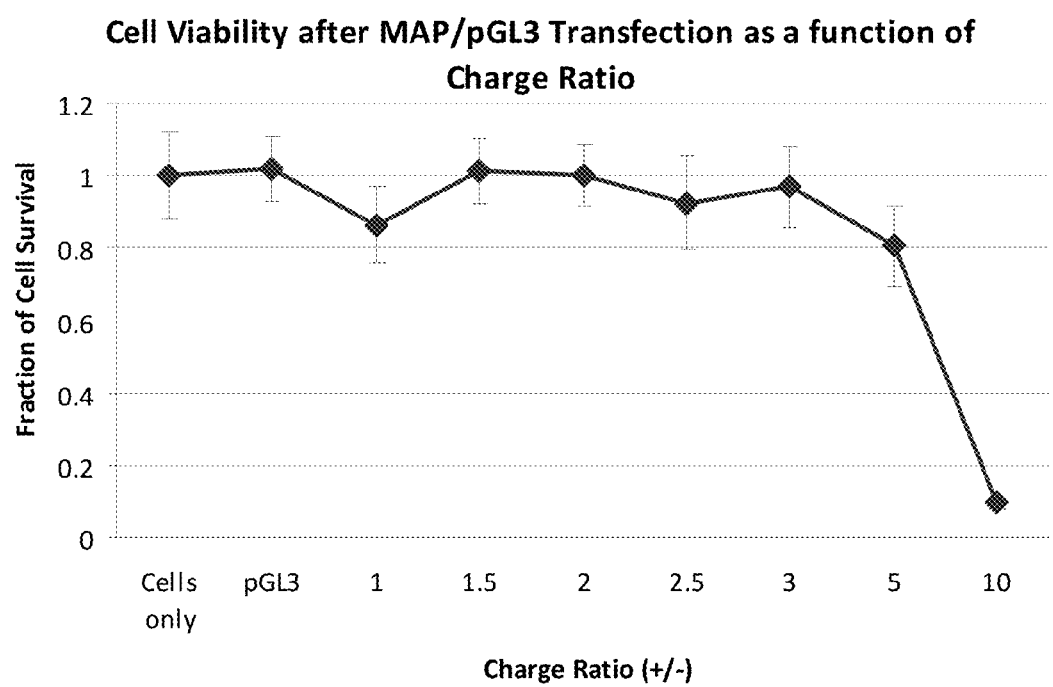
FIG. 9 shows delivery of an agent to a target with nanoparticles according to an embodiment herein described. In particular.

HeLa cells were seeded at 20,000 cells/well in 24 well plates 48 h prior to transfection and grown in medium supplemented with 10% FBS. MAP particles were formulated to contain 1 µg of pGL3 in 200 µL of Opti-MEM I at various charge ratios of polymer to pDNA (refer to Example 9). Growth medium was removed, cells washed with PBS and the particle formulation was added. The cells were subsequently incubated at 37° C. and 5% $CO_2$ for 5 h before the addition of 800 µL of growth medium supplemented with 10% FBS. After 48 h of incubation, a fraction of the cells were analyzed for cell viability using an MTS assay. The remaining cells were lysed in 100 µL of 1× Luciferase Cell Culture Lysis Reagent. Luciferase activity was determined by adding 100 µL of Luciferase Assay Reagent to 10 ul of cell lysate and bioluminescence was quantified using a Monolight luminometer. Luciferase activity is subsequently reported as relative light units (RLU) per 10,000 cells. Results are shown in FIG. 8 and FIG. 9.

Example 14

Co-Transfection of MAP/pDNA and/or siRNA Particles into HeLa Cells

Figure 10:
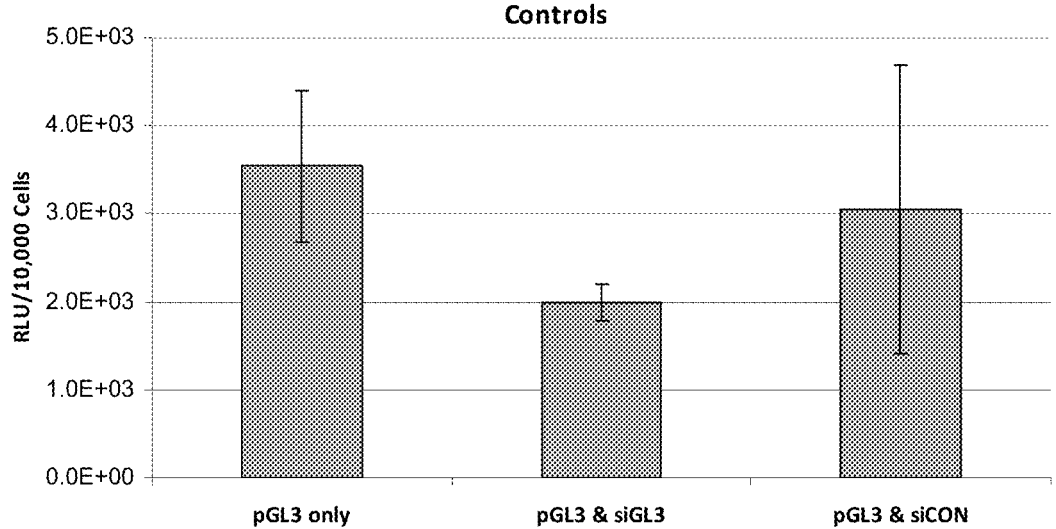
FIG. 10 shows delivery of multiple compounds to a target with nanoparticles according to an embodiment herein described. In particular.

HeLa cells were seeded at 20,000 cells/well in 24 well plates 48 h prior to transfection and grown in medium supplemented with 10% FBS. MAP particles were formulated to contain 1 µg of pGL3 and 50 nM of siGL3 in 200 µL of Opti-MEM I at a charge ratio of 5+/−. Particles containing only pGL3 or pGL3 and siCON were used as controls. Growth medium was removed, cells washed with PBS and the particle formulation was added. The cells were subsequently incubated at 37° C. and 5% $CO_2$ for 5 h before the addition of 800 µL of growth medium supplemented with 10% FBS. After 48 h of incubation, the cells were assayed for Luciferase activity and cell viability as described in Example 12. Results are shown in FIG. 10. Since the RLU is lowered in transfections with the siGL3 (correct sequence), both the siGL3 and the pGL3 must be co-delivered.

Example 15

Transfection of MAP/siGL3 into HeLa-LUC Cells

Figure 11:
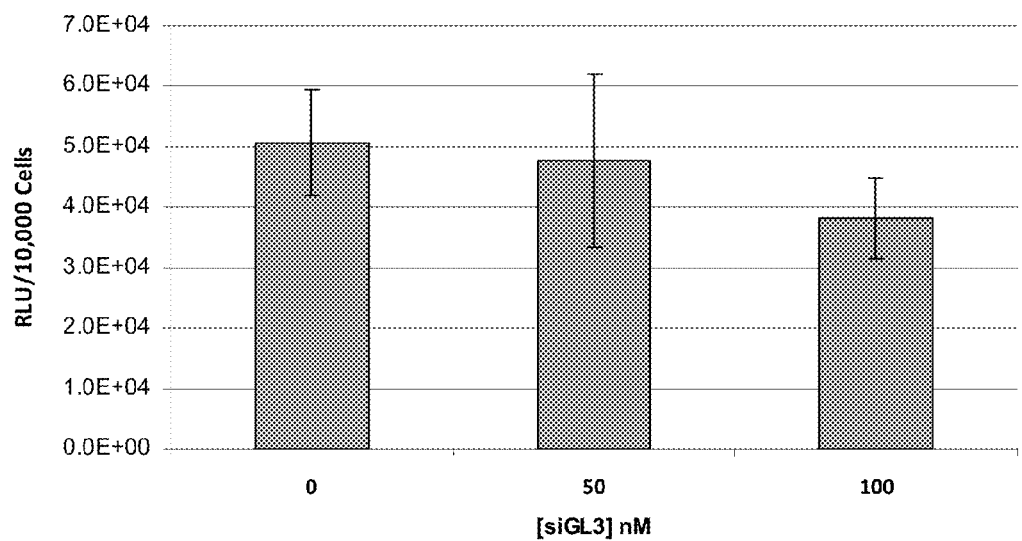
FIG. 11 shows delivery of a compound to a target with nanoparticles according to an embodiment herein described. In particular.

HeLa-LUC cells (contain gene encoding for the firefly luciferase protein) were seeded at 20,000 cells/well in 24 well plates 48 h prior to transfection and grown in medium supplemented with 10% FBS. MAP particles were formulated to contain 50 and 100 nM siGL3 in 200 µL of Opti-MEM I at a charge ratio of 5+/−. Growth medium was removed, cells were washed with PBS and the particle formulation was added. The cells were subsequently incubated at 37° C. and 5% $CO_2$ for 5 h before the addition of 800 µL of growth medium supplemented with 10% FBS. After 48 h of incubation, the cells were assayed for Luciferace activity and cell viability as described in Example 12. Results are shown in FIG. 11. Since the RLUs decline with increasing concentration of siGL3, these data suggest that inhibition of an endogenous gene can occur.

Example 16

Synthesis of Mucic Acid Diiodide, (10)

1 g (2.7 mmol) of mucic acid diamine (Example 3) was mixed with 3.8 mL (27.4 mmol) of triethylamine and 50 mL of anhydrous DMF prior to the dropwise addition of 1.2 mL (13.7 mmol) iodoacetylchloride in a 250 mL round bottom flask. This mixture was allowed to react overnight under constant stirring at room temperature. The solvent was subsequently removed by vacuum pump, the product filtered, washed with methanol and dried under vacuum to yield 0.8 g (1.3 mmol, 46%) of mucic acid diiodide. $^1$H NMR ($(CD_3)_2$SO) δ 8.20 (s 2H), 2H), 7.77 (s, 2H), 4.11 (m, 2H), 4.03 (m, 2H), 3.79 (m, 2H), 3.11-3.17 (m, 2H), 1.78 (d, 2H). ESI/MS (m/z): 652.8 $[M+Na]^+$

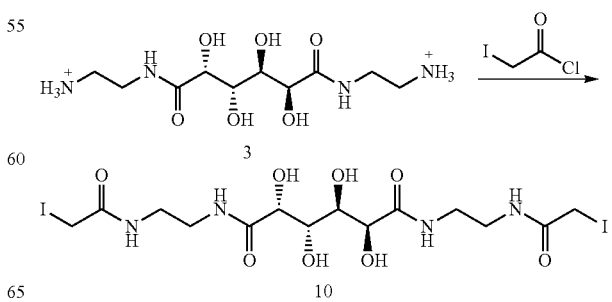

Example 17

Synthesis of Mucic Acid Dicysteine, (11)

To 7 mL of 0.1 M degassed sodium carbonate was added 17 mg of L-cysteine and 0.4 g of mucic acid diiodide. The resulting suspension was brought to reflux at 150° C. for 5 h until the solution turned clear. This mixture was then cooled to room temperature and adjusted to pH 3 via 1 N HCl. Slow addition of acetone was then employed for product precipitation. After filtration, washing with acetone and vacuum drying, 60 mg of crude product was obtained.

Example 18

Polymer Synthesis, (Poly(Mucic Acid-DiCys-PEG)) (12)

12 mg (21.7 μmol) of mucic acid dicysteine and 74 mg (21.7 μmol) of PEG-DiSPA 3400 were dried under vacuum prior to the addition of 0.6 mL of anhydrous DMSO under argon in a 2 neck 10 ml, round bottom flask. After 10 min of stirring, 9 μL (65.1 μmol) of anhydrous DIEA was transferred to the reaction vessel under argon. This mixture was stirred under argon overnight. The polymer containing solution was then dialyzed using a 10 kDa membrane centrifugal device and lyophilized to yield 47 mg (58%) of Poly(Mucic Acid-DiCys-PEG).

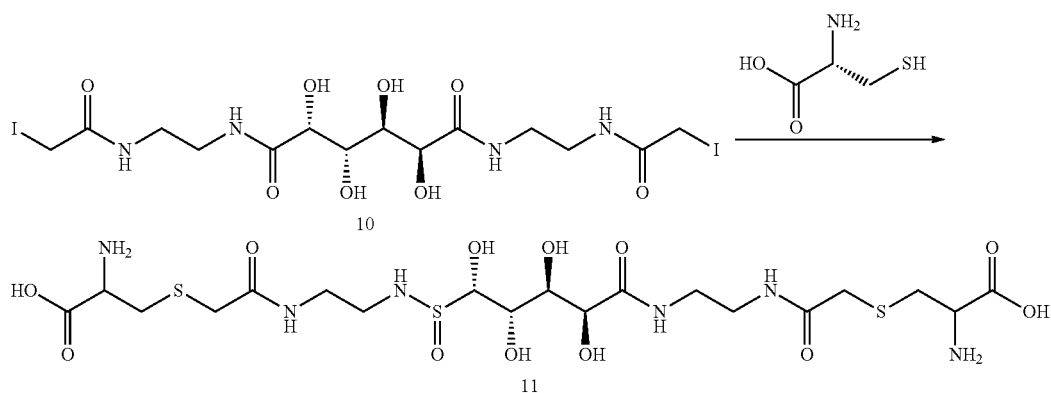

Example 17

Synthesis of Mucic Acid Dicysteine, (11)

To 20 mL of 0.1 M degassed sodium phosphate buffer at pH 7.5 in a 50 mL round bottom flask was added 0.38 g of L-cysteine (3.2 mmol) and 0.40 g (0.6 mmol) of mucic acid diiodine. The resulting suspension was allowed to reflux at 75° C. overnight, cooled to room temperature and lyophilized. 80 mL of DMF was subsequently added to this lyophilized light brown powder and separation of the insoluble excess reagent and phosphate salts from the soluble product was achieved by filtration. DMF was removed under reduced pressure and the product was vacuum dried to give 12 mg (0.02 mmol, 3%) of mucic acid dicysteine.

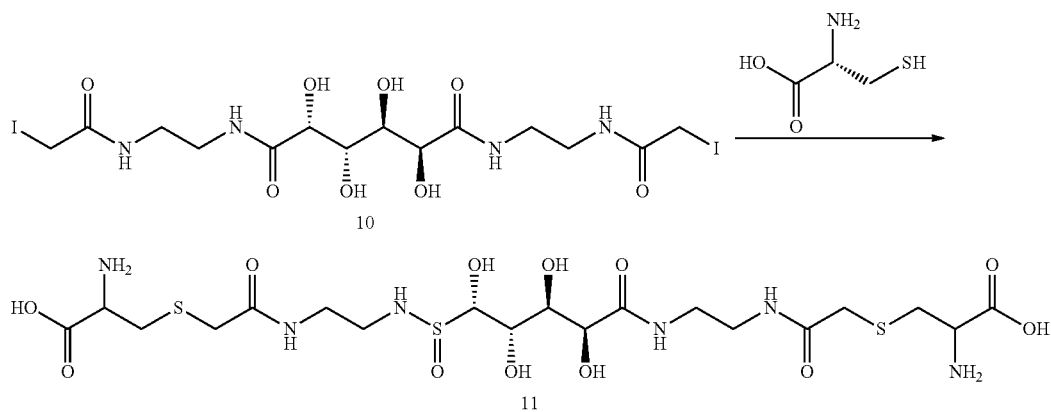

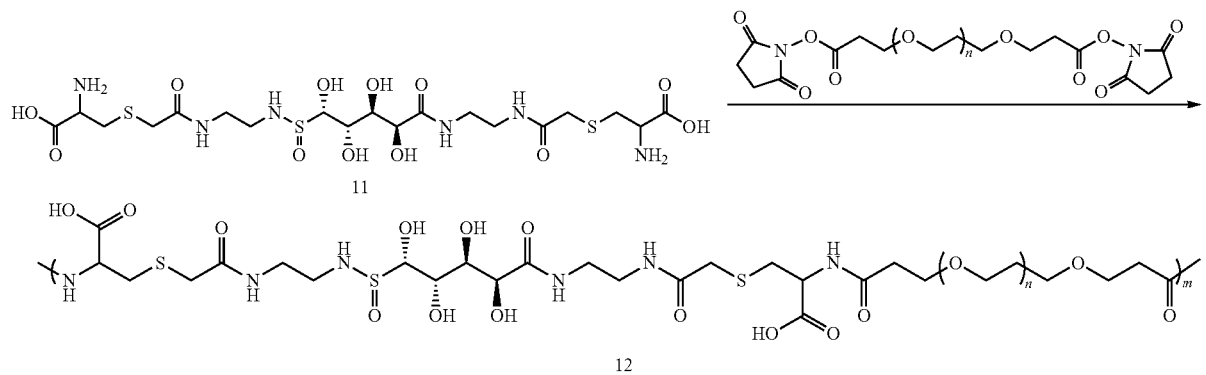

This polymer containing polyols is an anionic AB polymer.

Example 19

Covalent Attachment of Drug (Camptothecin, CPT) to Mucic Acid Polymer, (13)

10 mg (2.7 µmol of repeat units) of Poly(Mucic Acid-DiCys-PEG) was dissolved in 1.5 mL of anhydrous DMSO in a glass jar. After stirring for 10 min, 1.1 µL of DIEA (6.3 µmol), 3.3 mg (6.3 µmol) of TFA-Gly-CPT, 1.6 mg (8.1 µmol) of EDC and 0.7 mg (5.9 µmol) of NHS were added to the reaction mixture. After stirring for 8 hrs, 1.5 mL of ethanol was added and the solvents were removed under reduced pressure. The precipitate was dissolved in water and insoluble materials were removed by filtration through a 0.2 µm filter. The polymer solution was then dialyzed against water via a 10 kDa membrane and subsequently lyophilized to give the Poly (Mucic Acid-DiCys-PEG)-CPT conjugate.

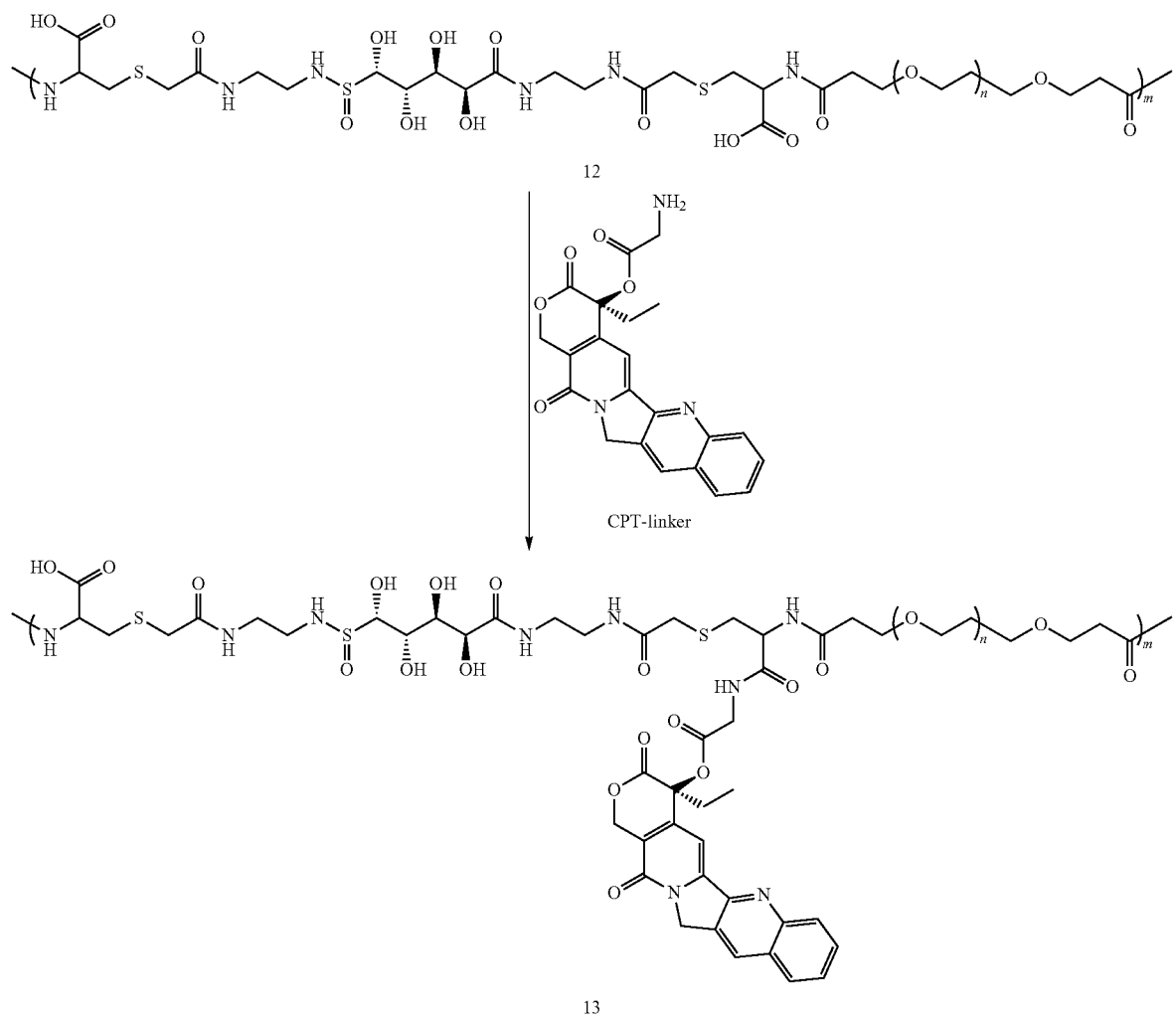

Example 20

Formulation of Nanoparticle with CPT-Mucic Acid Polymer (13) in Water, (20)

The Effective diameters of poly(Mucic Acid-DiCys-PEG) and poly(Mucic Acid-DiCys-PEG)-CPT conjugate were measured by formulating the polymers in double distilled water (0.1-10 mg/mL) and evaluated via dynamic light scattering (DLS) using a ZetaPALS (Brookhaven Instrument Co) Instrument. 3 successive runs of 1 min each were subsequently recorded and averaged. The zeta potentials of both compounds was measured in a 1.1 mM KCl solution using a ZetaPALS (Brookhaven Instrument Co) Instrument. 10 successive automated runs at target residuals of 0.012 were then performed and results averaged (FIG. 14). In particular, there two distributions were measured for the poly(Mucic Acid-DiCys-PEG)-CPT conjugate the predominant distribution was a 57 nm (60% of the total particle population). A second minor distribution was also was measured at 233 nm.

Example 21

Formulation of Boronic Acid-PEGylated Nanoparticle with CPT-Mucic Acid Polymer (13) and Boronic Acid-Disulfide-PEG$_{5000}$ (6) in Water The boronic acid PEGylated poly(Mucic Acid-DiCys-PEG)-CPT nanoparticle is formulated by dissolving the polymer in double distilled water at a concentration of 0.1 mg/mL followed by the addition of Polymer 6 (BA-PEG) also in water, such that the ratio of BA-PEG to the diols on the mucic acid sugar in the poly(Mucic Acid-DiCys-PEG)-CPT conjugate is 1:1. The mixture is incubated for 30 mins after which the effective diameter and zeta potential are measured using a ZetaPALS (Brookhaven Instrument Co) instrument.

Example 22

Targeted Nanoparticles for pDNA Delivery in Mice

The plasmid pApoE-HCRLuc contains the gene to express luciferase and is under the control of a liver specific promoter. Polymer (MAP) 4 (0.73 mg), polymer 6 (73 mg) and polymer 9 (0.073 mg) were combined in 5 mL of water and then 1.2 mL of water containing the pApoE-HCRLuc plasmid were added (gives a charge ratio of polymer 4 to the plasmid of +3). The particles were placed in D5W (5% glucose in water) by successive spin filtering with subsequent additions of D5W (starting from the initial formulation that was in water). Nude mice were implanted with Hepa-1-6 liver cancer cells and tumors were allowed to grow until a size of approximately 200 mm$^3$. Injections of the targeted nanoparticles were done i.v. in the tail vein at an amount equal to 5 mg plasmid/kg mouse. The mice were imaged 24 hours after the injections. The mice showed no signs of toxicity and there was luciferase expression detected in the region of the tumor and not in the region of the liver.

The examples set forth above are provided to give those of ordinary skill in the art a complete disclosure and description of how to make and use the embodiments of the particles, compositions, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Summary, Detailed Description, and Examples is hereby incorporated herein by reference.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Although any methods and materials similar or equivalent to those described herein can be used in the practice for testing of the specific examples of appropriate materials and methods are described herein.

A number of embodiments of the disclosure have been described. Nevertheless, it will be understood that various modifications may be made without departing from the spirit and scope of the present disclosure. Accordingly, other embodiments are within the scope of the following claims.

REFERENCES

Davis Mark E., Chen Zhuo (Georgia) and. Shin Dong M "Nanoparticle therapeutics: an emerging treatment modality for cancer" in Nature 2008 vol. 7, pages 771-782

Duncan Ruth "Polymer conjugates as anticancer nanomedicines" Nature 2006 vol. 6, pages 688-701

Allen Theresa. M "Ligand-Targeted Therapeutics In Anticancer Therapy" in Nature 2002 vol. 2 pages 750-763

Liu Yemin and Reineke Theresa M. "Hydroxyl Stereochemistry and Amine Number within Poly(glycoamidoamine)s Affect Intracellular DNA Delivery" in J. Am. Chem. Soc. 2005, 127, 3004-3015

What is claimed is:

1. A polymer conjugate comprising a boronic acid of formula:

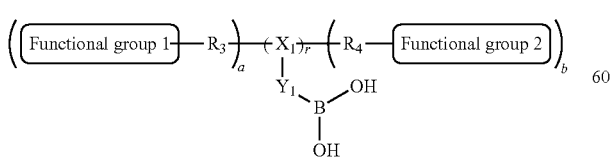

(XXX)

wherein $R_3$ and $R_4$ are independently $(CH_2CH_2O)_t$, where t is from 2 to 2000, $X_1$ is —NH—C(=O)—, —C(=O)—NH—CH$_2$, —C(=O)—NH—, —S—S—, —O—C(=O)— or —C(=O)—O—;

$Y_1$ is an alkylene with a carbon number of at least 1 or is an aromatic group;

Functional group 1 and Functional group 2 are the same or different and independently comprise —OCH$_3$, —OH, —B(OH)$_2$, —COOH, —NH$_2$, or —(X$_1$)—(Y$_1$)—B(OH)$_2$;

r is in a range of from 1 to 1000;

a is 0, 1, 2, or 3; and b is 1, 2 or 3; and a polyol polymer having a repeating structure of:

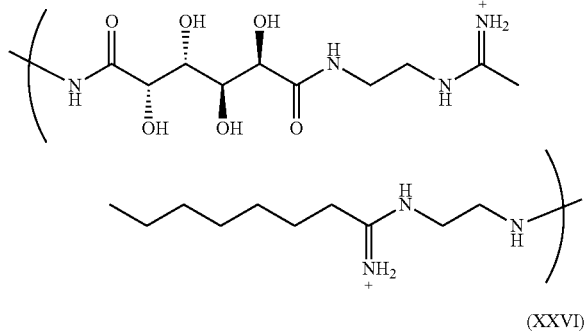

(XXV)

(XXVI)

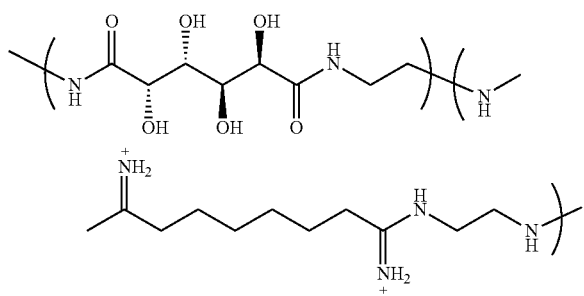

(XXVII)

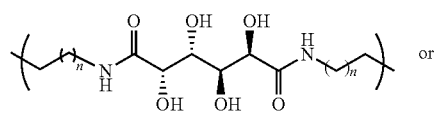 or (XXVIII)

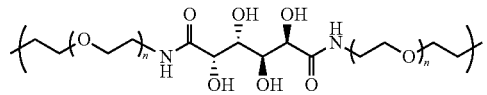

where n is from 1 to 20, wherein the boronic acid polymer is coupled to the polyol polymer with at least one reversible borate ester linkage that replaces the hydroxyl groups of the $Y_1$—$B(OH)_2$ moiety.

2. The polymer conjugate of claim 1, wherein $Y_1$ is phenyl.

3. The polymer conjugate of claim 1, wherein t is from 100 to 300.

4. The polymer conjugate of claim 1, wherein r is 1, a is 0, and b is 1.

5. The polymer conjugate of claim 1, wherein Functional group 1 and Functional group 2 are the same or different and independently comprise —COOH, —NH$_2$, —OH, or —B(OH)$_2$.

6. The polymer conjugate of claim 1 wherein:

$Y_1$ is phenyl;
a is 0;
b is 1;
r is 1;
t is 20 to 300; and
Functional group 2 comprises —OH, —B(OH)$_2$, —COOH, or —NH$_2$.

7. The polymer conjugate of claim 1, wherein at least a portion of the boron atoms comprise $^{10}$B.

8. The polymer conjugate of claim 1, wherein $Y_1$ is an aromatic group comprising at least one $^{19}$F, the polymer being detectable by in vivo imaging via $^{19}$F NMR spectroscopy when in a patient.

9. The polymer conjugate of claim 1, wherein $Y_1$ is an aromatic group comprising at least one $^{18}$F.

10. A polymer conjugate of claim 1 and at least one targeting ligand, wherein the boronic acid polymer is coupled to the targeting ligand with at least one reversible linkage with the OH, —B(OH)$_2$, —COOH, or —NH$_2$ of at least one of Functional group 1 or Functional group 2, the at least one targeting ligand comprising a nucleotide, polynucleotide, peptide, polypeptide, protein, full antibody, antibody fragment, polysaccharide, or small molecule.

11. The polymer conjugate of claim 10, wherein the small molecule comprises transferrin, folic acid, or galactose.

12. The polymer conjugate of claim 10, wherein the small molecule comprises chemotherapeutics including an epothilone, a camptothecin-based drugs, doxorubicin, taxol, or a nucleic acid.

13. A polymer conjugate comprising a boronic acid of formula:

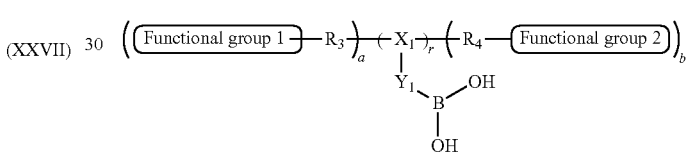

(XXX)

wherein $R_3$ and $R_4$ are independently (CH$_2$CH$_2$O)$_t$, where t is from 2 to 2000, $X_1$ is —NH—C(=O)—, —C(=O)—NH—CH$_2$, —C(=O)—NH—, —S—S—, —O—C(=O)— or —C(=O)—O—;

$Y_1$ is an alkylene with a carbon number of at least 1 or is an aromatic group;

Functional group 1 and Functional group 2 are the same or different and independently comprise —OCH$_3$, —OH, —B(OH)$_2$, —COOH, —NH$_2$, or —(X$_1$)—(Y$_1$)—B(OH)$_2$;

r is in a range of from 1 to 1000;

a is 0, 1, 2, or 3; and b is 1, 2 or 3; and a polyol polymer having at least one of the following repeating structural units:

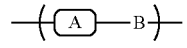

(I)

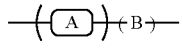

(II)

(III)

wherein

A is an organic moiety of having a structure of:

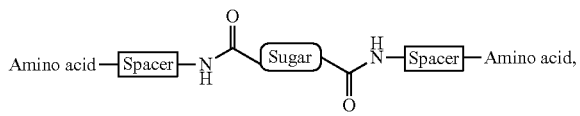

VI wherein
the spacer is independently selected from any organic group;
the amino acid is selected from any organic group bearing a free amine and a free carboxylic acid group;
n is a number from 1 to 20; and
$Z_1$ is independently selected from —$NH_2$, —OH, —SH, and —COOH.

14. The polymer conjugate of claim 13, wherein A is independently:

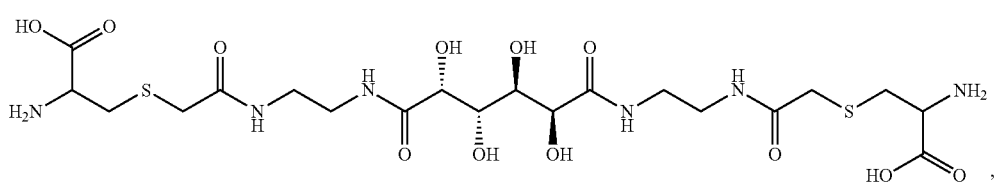

IX

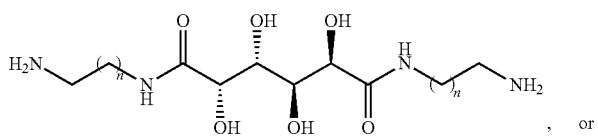

X

, or

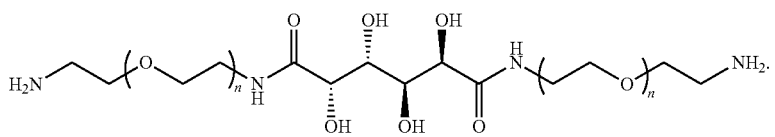

XI

-continued

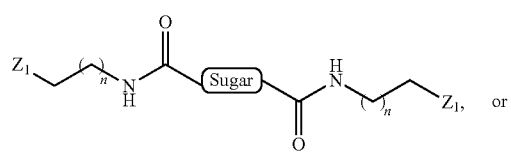

VII

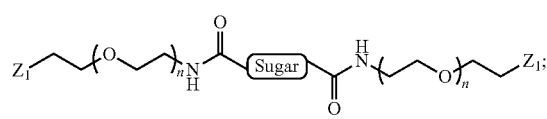

VIII

15. The polymer conjugate of claim 13, wherein B is

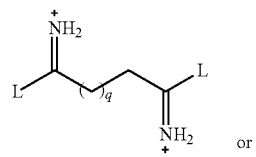

(XXIII)

or

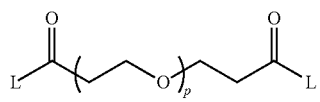

(XIV)

in which q is 1-20; p is 20-200; and L is a leaving group.

16. The polymer conjugate of claim 13, wherein the structural unit of formula (I) is:

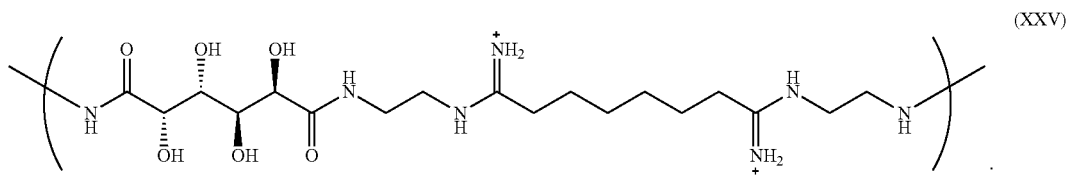

(XXV)

17. The polymer conjugate of claim 13, wherein the structural unit of formula (II) is:

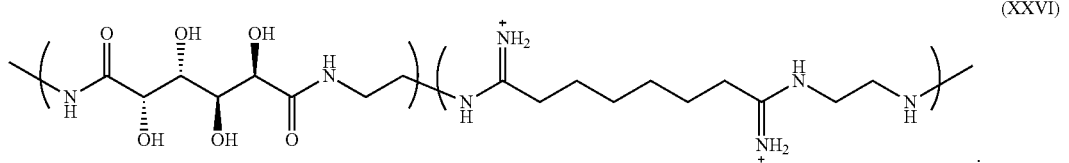

(XXVI)

18. The polymer conjugate of claim 13, wherein the structural unit of formula (III) is:

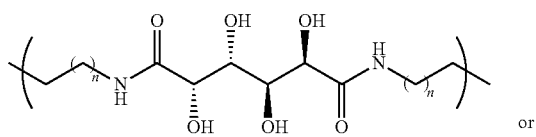

(XXVII)

or

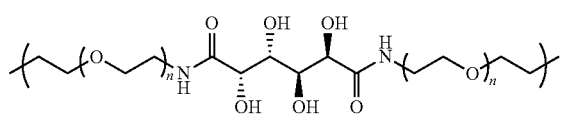

(XXVIII)

in which n is 1-20.

19. The polymer conjugate of claim 13, wherein the polymer containing a polyol is

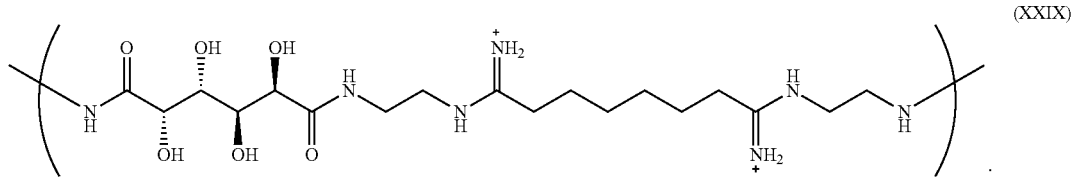

(XXIX)

20. The polymer conjugate of claim 13, further comprising a targeting ligand, wherein the boronic acid polymer is coupled to the targeting ligand with at least one reversible linkage with the OH, —B(OH)$_2$, —COOH, or —NH$_2$ of at least one of Functional group 1 or Functional group 2, the targeting ligand comprising at least one a small molecule, protein, protein fragment, peptide, full antibody, antibody fragment, monosaccharide, polysaccharide, nucleotide, or polynucleotide.

21. The polymer conjugate of claim 20, wherein the targeting ligand is an antibody or antibody fragment against a surface cell receptor.

22. The polymer conjugate of claim 20, wherein the targeting ligand is folic acid.

23. The polymer conjugate of claim 20, wherein the targeting ligand is transferrin.

24. The polymer conjugate of claim 13, further comprising a therapeutic agent, wherein the boronic acid polymer is coupled to the therapeutic agent with at least one reversible linkage with the OH, —B(OH)$_2$, —COOH, or —NH$_2$ of at least one of Functional group 1 or Functional group 2.

25. The polymer conjugate of claim 24, wherein the therapeutic agent comprises at least one of a chemotherapeutic or a nucleic acid.

26. The polymer conjugate of claim 25, wherein the therapeutic agent comprises camptothecin, doxorubicin, or taxol.

* * * * *

SEQUENCE LISTING

<160> NUMBER OF SEQ ID NOS: 4

<210> SEQ ID NO 1
<211> LENGTH: 21
<212> TYPE: DNA

```
<213> ORGANISM: Artificial Sequence
<220> FEATURE:
<223> OTHER INFORMATION: Description of Artificial Sequence: Synthetic
      oligonucloetide
<220> FEATURE:
<223> OTHER INFORMATION: Description of Combined DNA/RNA Molecule:
      Synthetic oligonucloetide

<400> SEQUENCE: 1
gugccagagu ccuucgauat t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucloetide
<220> FEATURE:
<223> OTHER INFORMATION: Description of Combined DNA/RNA Molecule:
      Synthetic oligonucloetide

<400> SEQUENCE: 2
uaucgaagga cucuggcact t                                              21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
uagcgacuaa acacaucaau u                                              21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uugauguguu uagucgcuau u                                              21
```